(12) United States Patent
Bjork et al.

(10) Patent No.: US 11,827,754 B2
(45) Date of Patent: Nov. 28, 2023

(54) FIBRIN COMPOSITION COMPRISING CARRIER MATERIAL, METHOD AND WOUND ARTICLES

(71) Applicant: 3M INNOVATIVE PROPERTIES COMPANY, Saint Paul, MN (US)

(72) Inventors: Jason W. Bjork, Cottage Grove, MN (US); Amy S. Determan, Mahtomedi, MN (US); Jonathan J. O'Hare, Oakdale, MN (US); Robert A. Asmus, Hudson, WI (US); James P. Dizio, Saint Paul, MN (US); Zhicheng Tian, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 1011 days.

(21) Appl. No.: 16/338,776

(22) PCT Filed: Oct. 4, 2017

(86) PCT No.: PCT/US2017/055022
§ 371 (c)(1),
(2) Date: Apr. 2, 2019

(87) PCT Pub. No.: WO2018/067628
PCT Pub. Date: Apr. 12, 2018

(65) Prior Publication Data
US 2021/0324150 A1 Oct. 21, 2021

Related U.S. Application Data

(60) Provisional application No. 62/404,491, filed on Oct. 5, 2016.

(51) Int. Cl.
*C08J 3/075* (2006.01)
*C08L 89/00* (2006.01)

(52) U.S. Cl.
CPC ............... *C08J 3/075* (2013.01); *C08L 89/00* (2013.01); *C08J 2389/00* (2013.01); *C08J 2439/04* (2013.01)

(58) Field of Classification Search
CPC ......... C08J 3/075; C08J 2389/00; C08L 89/00
See application file for complete search history.

(56) References Cited

U.S. PATENT DOCUMENTS

| | | |
|---|---|---|
| 2,492,458 A | 12/1949 | Bering, Jr. |
| 2,736,721 A | 2/1956 | Dexter |

(Continued)

FOREIGN PATENT DOCUMENTS

| | | |
|---|---|---|
| CA | 2288539 | 5/2000 |
| EP | 1695724 | 8/2006 |

(Continued)

OTHER PUBLICATIONS

W. L. J. Hinrichs et al., "Fabrication and Characterization of an Asymmetric Polyurethane Membrane for Use as a Wound Dressing," 3 Journal of Applied Biomaterials 287-303 (1992) (Year: 1992).*

(Continued)

*Primary Examiner* — Robert S Jones, Jr.
*Assistant Examiner* — Jiangtian Xu
(74) *Attorney, Agent, or Firm* — 3M Innovative Properties Company

(57) ABSTRACT

Provided is a method of forming a fibrin hydrogel composition, the method including providing a fibrin hydrogel or precursor thereof, comprising fibrin hydrogel forming salt. The fibrin hydrogel forming salt concentration is greater than or equal to the threshold concentration to form a fibrin hydrogel. The method further includes combining the fibrin hydrogel with a carrier material. The concentration of the carrier material typically ranges from 0.1 to about 50 wt.-%.

(Continued)

The method further includes reducing the salt concentration below the threshold concentration to form a fibrin hydrogel.

20 Claims, 3 Drawing Sheets

(56) References Cited

U.S. PATENT DOCUMENTS

| | | | |
|---|---|---|---|
| 2,958,608 A | 11/1960 | Barnard |
| RE24,906 E | 12/1960 | Ulrich |
| 3,037,455 A | 6/1962 | Bozimowski |
| 3,389,827 A | 6/1968 | Abere |
| 4,112,213 A | 9/1978 | Waldman |
| 4,158,594 A | 6/1979 | Becker |
| 4,310,509 A | 1/1982 | Berglund |
| 4,323,557 A | 4/1982 | Rosso |
| 4,427,650 A | 1/1984 | Stroetmann |
| 4,442,655 A | 4/1984 | Stroetmann |
| 4,453,939 A | 6/1984 | Zimmerman |
| 4,472,480 A | 9/1984 | Olson |
| 4,548,736 A | 10/1985 | Muller |
| 4,595,001 A | 6/1986 | Potter |
| 4,710,270 A | 12/1987 | Sunden |
| 4,833,179 A | 5/1989 | Young |
| 4,871,812 A | 10/1989 | Lucast |
| 4,931,282 A | 6/1990 | Asmus |
| 5,088,483 A | 2/1992 | Heinecke |
| 5,120,781 A | 6/1992 | Johnson, Jr. |
| 5,160,315 A | 11/1992 | Heinecke |
| 5,214,119 A | 5/1993 | Leir |
| 5,225,473 A | 7/1993 | Duan |
| 5,389,376 A | 2/1995 | Duan |
| 5,409,966 A | 4/1995 | Duan |
| 5,531,855 A | 7/1996 | Heinecke |
| 5,849,325 A | 12/1998 | Heinecke |
| 5,908,693 A | 6/1999 | Delgado |
| 5,989,215 A | 11/1999 | Delmotte |
| 6,074,663 A | 6/2000 | Delmotte |
| 6,083,856 A | 7/2000 | Joseph |
| 6,171,985 B1 | 1/2001 | Joseph |
| 6,198,016 B1 | 3/2001 | Lucast |
| 6,264,976 B1 | 7/2001 | Heinecke |
| 6,310,267 B1 | 10/2001 | Rapp |
| 6,441,092 B1 | 8/2002 | Gieselman |
| 6,486,377 B2 | 11/2002 | Rapp |
| 6,500,427 B1 | 12/2002 | Heimburger |
| 6,503,527 B1 | 1/2003 | Whitemore |
| 6,503,731 B2 | 1/2003 | Marx |
| 6,518,343 B1 | 2/2003 | Lucast |
| 6,548,727 B1 | 4/2003 | Swenson |
| 6,552,172 B2 | 4/2003 | Marx |
| 6,599,515 B1 | 7/2003 | Delomtte |
| 6,699,484 B2 | 3/2004 | Whitemore |
| 6,965,014 B1 | 11/2005 | Delmotte |
| 7,407,709 B2 | 8/2008 | Zhou |
| 7,714,107 B2 | 5/2010 | Yayon |
| 8,193,317 B2 | 6/2012 | Yayon |
| 8,273,372 B2 | 9/2012 | Dye |
| 8,445,009 B2 | 9/2013 | MacPhee |
| 8,529,941 B2 | 9/2013 | Hakimimehr |
| 8,618,258 B2 | 12/2013 | Yayon |
| 9,072,681 B2 | 7/2015 | Hakimimehr |
| 9,278,155 B2 | 3/2016 | Asmus |
| 10,137,222 B2 * | 11/2018 | Bjork | A61P 17/02 |
| 2001/0025154 A1 | 9/2001 | Rapp |
| 2007/0148474 A1 | 6/2007 | Lier |
| 2008/0033333 A1 | 2/2008 | MacPhee |
| 2010/0291219 A1 | 11/2010 | Karp |
| 2011/0071079 A1 | 3/2011 | Ameer |
| 2011/0206923 A1 | 8/2011 | Liu |
| 2011/0206924 A1 | 8/2011 | Liu |
| 2011/0212325 A1 | 9/2011 | Determan |
| 2013/0040073 A1 | 2/2013 | Pett |
| 2014/0369991 A1 * | 12/2014 | Schutte | A61K 47/10 |
| | | | 424/94.64 |
| 2015/0030580 A1 | 1/2015 | Seliktar |
| 2015/0297806 A1 | 10/2015 | Hakimimehr |
| 2016/0024141 A1 | 1/2016 | Issa |

FOREIGN PATENT DOCUMENTS

| | | |
|---|---|---|
| WO | WO 1997-044015 | 11/1997 |
| WO | WO 1999-25782 | 5/1999 |
| WO | WO 2002-089868 | 11/2002 |
| WO | WO 2003-035115 | 5/2003 |
| WO | WO 2004-067704 | 8/2004 |
| WO | WO 2007-144644 | 12/2007 |
| WO | WO 2008-036255 | 3/2008 |
| WO | WO 2009-083544 | 7/2009 |
| WO | WO 2009-120433 | 10/2009 |
| WO | WO 2010-058132 | 5/2010 |
| WO | WO 2010-136818 | 12/2010 |
| WO | WO 2014-209620 | 12/2014 |
| WO | WO 2015-097687 | 7/2015 |
| WO | WO 2015-124732 | 8/2015 |
| WO | WO 2016-160541 | 10/2016 |
| WO | WO 2018-067622 | 4/2018 |

OTHER PUBLICATIONS

"Hofmeister Series", From Wikipedia—The Free Encyclopedia, [retrieved from the internet on May 28, 2019], URL <http://en.wikipedia.org/wiki/Hofmeister_series>, 2 pages.
Conductivity Ordering Guide, 1999, 2 pages.
Dastjerdi, "Cohesive Behavior of Soft Biological Adhesives: Experiments and Modelling", Acta Biomaterialia, Sep. 2012, vol. 8, No. 9, pp. 3349-3359.
Electrical Conductivity of Aqueous Solutions, 1 page.
Janmey, "Fibrin Gels and Their Clinical and Bioengineering Applications", Journal of the Royal Society Interface, Jan. 2009, vol. 6, No. 30, pp. 1-10.
Laurens, "Fibrin Structure and Wound Healing", Journal of Thrombosis and Haemostasis, Apr. 2006, vol. 4, No. 5, pp. 932-939.
Molyneux, Water—Soluble Polymers: Properties and Behavior, 151-152, (1983).
Morena-Arotzena, "Characterization of Fibrin and Collagen Gels of Engineering Wound Healing Models," Materials (Basel), Apr. 2015, vol. 8, No. 4, pp. 1636-1651.
Plasdone povidones, Ashland, 4 pages.
Polyvinylpyrolidone (PVP) Plolymer, Ashland Technical Information, Bulletin VC-843, 9 pages.
International Search Report for PCT International Application No. PCT/US2017/55022, dated Nov. 29, 2017, 3 pages.

* cited by examiner

FIBRIN COMPOSITION COMPRISING CARRIER MATERIAL, METHOD AND WOUND ARTICLES

CROSS REFERENCE TO RELATED APPLICATIONS

This application is a national stage filing under 35 U.S.C. 371 of PCT/US2017/055022, filed Oct. 4, 2017, which claims the benefit of U.S. Provisional Application No. 62/404,491, filed Oct. 5, 2016, the disclosures of which are incorporated by reference in their entirety herein.

BACKGROUND

Fibrinogen is cleaved and polymerized into fibrin using thrombin in a well-characterized process. Thrombin cleaves fibrinogen, forming fibrin monomers. Once fibrinogen is cleaved, fibrin monomers come together and form a covalently crosslinked fibrin network in the presence of factors, such as Factor XIII, normally present in blood. At a wound site, the fibrin network helps to close the wound and promote healing.

Various attempts have been made to provide fibrin in a form useful for treating wounds. Perhaps the most commonly known is the in situ generation of fibrin glue, typically performed by delivering separate solutions of fibrinogen and thrombin from a dual-barrel syringe.

International Patent Publication No. WO 97/44015 (Heath et al.) describes soluble microparticles including fibrinogen or thrombin, in free-flowing form. It is stated that these microparticles can be mixed to give a dry powder, to be used as a fibrin sealant that is activated only at a wound site.

U.S. Pat. No. 6,486,377 B2 (Rapp et al.) describes a biodegradable, flexible wound covering based on fibrin and a process for its preparation, in which a fibrinogen solution is subjected to a single-stage or multi-stage dialysis, then a flexible fibrin web is formed by action of a thrombin solution on the fibrinogen solution and this is subsequently subjected to freeze-drying.

International Patent Publication No. WO 2009/120433 A2 (Delmotte et al.) describes a fibrin material and method for producing the same.

WO2014/209620 describes a fibrin-coated wound dressing articles.

SUMMARY

In one embodiment, a method of forming a fibrin hydrogel composition is described. The method comprises providing a fibrin hydrogel or precursor thereof, comprising fibrin hydrogel forming salt. The fibrin hydrogel forming salt concentration is greater than or equal to the threshold concentration to form a fibrin hydrogel. The method further comprises combining the fibrin hydrogel with a carrier material. The concentration of the carrier material typically ranges from 0.1 to about 50 wt.-%. The method further comprises reducing the salt concentration below the threshold concentration to form a fibrin hydrogel. The step of reducing the salt concentration can occur before and/or after combining the fibrin hydrogel with the carrier material. The fibrin hydrogel precursor may comprise an aqueous solution comprising fibrinogen, fibrin-forming enzyme, and a fibrin hydrogel forming salt. The salt typically comprises a calcium salt in combination with other fibrin hydrogel forming salts such as NaCl. The threshold salt concentration of the aqueous solution is at least 0.45 wt.-%, or 0.50 wt.-%, or 0.6 wt.-%, or 0.7 wt.-%, or 0.8 wt.-% or 0.9 wt.-%. In some embodiments, the aqueous solution further comprises a fibrin hydrogel plasticizer.

In another embodiment, a fibrin composition is described comprising a fibrin hydrogel having a fibrin concentration ranging from 0.1 to 15 wt.-%; carrier material, and a fibrin hydrogel forming salt. The concentration of the carrier material typically ranges from 0.1 to about 50 wt.-%. The fibrin hydrogel forming salt has a concentration less than a threshold concentration to form the fibrin hydrogel. In typical embodiments, the fibrin hydrogel is at least partially dehydrated.

In another embodiment, a fibrin composition is described comprising a dehydrated fibrin hydrogel interdispersed with 0.5 to 99 wt.-% of a carrier material; wherein the carrier material is not water, plasticizer, or a mixture thereof and the fibrin composition comprises salt at a concentration no greater than 20 wt.-%.

The fibrin composition and dehydrated fibrin hydrogel typically has a salt concentration no greater than 20, 15, 10, or 5 wt.-%. The fibrin hydrogel or fibrin composition can be in various physical forms such a sheet, foam, or plurality of pieces.

The carrier material is not water, fibrin hydrogel plasticizer, or mixture thereof. In some embodiments, the carrier material is a polymer. The carrier material may optionally further comprises a swelling agent and/or a modifying polymer.

In another embodiment, a method of forming a fibrin article is described comprising providing a (e.g. dehydrated) fibrin composition as described herein and disposing the fibrin composition on or within a carrier layer such as a release liner, a polymeric film, a polymeric foam, or a nonwoven or woven fibrous material.

In other embodiments, wound dressings are described comprising a fibrin composition as described herein alone or in combination with a carrier material.

In another embodiment, a method of treatment of a wound is described comprising providing a fibrin composition or wound dressing as described herein, and providing the fibrin composition proximate a wound. The fibrin composition can increase the rate of re-epithelialization and/or wound healing biological markers such as VEGF, EGF, MMP1, MMP8, MMP9, and TIMP-1.

DETAILED DESCRIPTION

Figure 1:
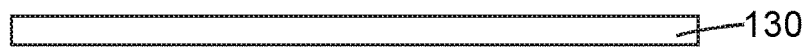
FIG. 1 is a schematic cross-section of an illustrative embodiment of a fibrin article suitable for a wound dressing comprising a fibrin composition in the form of a sheet.

In one embodiment, a method of forming a fibrin hydrogel composition is described. As used herein, "fibrin" refers to a protein formed by the reaction of fibrinogen with a fibrin-forming enzyme (e.g. thrombrin). Such enzyme is capable of cleaving fibrin A and B peptides from fibrinogen and convert it to fibrin. Fibrinogen is a precursor to fibrin.

The method comprises providing a fibrin hydrogel or precursor thereof, comprising fibrin hydrogel forming salt.

The precursor thereof typically comprises an aqueous solution comprising fibrinogen, a fibrin-forming enzyme and salt. Thrombin is the most common fibrin-forming enzyme. Alternative fibrin-forming enzymes include batroxobin, crotalase, ancrod, reptilase, gussurobin, recombinant thrombin-like enzymes, as well as venom of 20 to 30 different species of snakes. The fibrin-forming enzyme can be any one or combination of such fibrin-forming enzymes.

Any suitable sources of fibrinogen and thrombin can be used in the preparation of the fibrin hydrogel. For example, the species from which the fibrinogen is obtained could be human, bovine, porcine, or other animal sources. Similarly, thrombin can also be obtained from human, bovine, porcine, or other animal sources. Both fibrinogen and thrombin can also be obtained from recombinant sources. Fibrinogen and thrombin can be obtained commercially as aqueous solutions, and the concentrations of these solutions may vary. Alternatively, fibrinogen and thrombin can be provided in lyophilized form and stored at very low temperatures. Lyophilized fibrinogen is typically reconstituted with sterile water before use. Thrombin is also reconstituted with sterile calcium chloride and water before use. Saline, phosphate buffered solution, or other reconstituting liquid can also be used. In preparing fibrin, the reconstituted fibrinogen and thrombin are then combined to form fibrin.

The aqueous solution generally comprises a sufficient amount of fibrinogen and fibrin-forming enzyme (e.g. thrombin) to produce the desired amount of fibrin. In some embodiments, the amount of fibrinogen in the aqueous solution is at least 1 mg/mL and typically no greater than 100, 120, 130, 140, or 150 mg/mL (e.g. 15 wt-%). In some embodiments, the amount of fibrinogen is no greater than 75, 50, 25, 20, 15, 10 or 5 mg/mL. Further, the amount of fibrin-forming enzyme (e.g. thrombin) in the aqueous solution is at least 0.01, 0.02, 0.03, 0.04, or 0.05 Units/milliliter (U/mL) and typically no greater than 500 U/mL. In some embodiments, the amount of fibrin-forming enzyme (e.g. thrombin) in the aqueous solution is no greater than 250, 125, 50, 25, 20, 15, 10, or 5, 4, 3, 2, or 1 U/mL. Aqueous solutions of fibrinogen typically comprise salt (e.g. saline). The salt concentration is sufficient such that the fibrinogen forms a solution. Alternatively, solid fibrinogen can be reconstituted in saline or other salt solution. In a typical embodiment, substantially all the fibrinogen is converted to fibrin. Excess fibrin-forming enzyme (e.g. thrombin) is removed when the fibrin hydrogel is rinsed to reduce the salt content.

The aqueous solution further comprises salt suitable for producing a fibrin containing hydrogel. Thus, such salt can be characterized as a fibrin hydrogel forming salt. The fibrin is generally uniformly dispersed and soluble in the hydrogel. Hence, the hydrogel typically contains little or no fibrin precipitates. When a fibrin hydrogel is formed, the hydrogel is generally a continuous two-phase system that can be handled as a single mass.

Various salts with Group I and/or Group II metal cations have been utilized to solubilize protein such as potassium, sodium, lithium, magnesium, and calcium. Other cations utilized in protein synthesis include citrate, ammonium and guanidinium.

Various anions have also been utilized to solubilize protein. Although chloride anion is most common, nitrate and acetate are most similar to chloride according to the Hofmieister series, i.e. a classification of ions in order of their ability to salt out (e.g. precipitate) or salt in (e.g. solubilize) proteins.

In some embodiments, the salt comprises sodium chloride. The amount of sodium chloride in the aqueous solution and fibrin hydrogel, prior to dehydration, is typically greater than 0.09 wt.-% of the solution. The concentration of sodium chloride may be at least 0.10, 0.20, 0.30, 0.04, 0.50, 0.60, 0.70, 0.80 or "normal saline" 0.90 wt.-% and typically no greater than 1 wt.-%. Minimizing the salt concentration is amenable to minimizing the salt that is subsequently removed.

The salt typically comprises a calcium salt, such as calcium chloride. The amount of calcium salt in the aqueous solution and fibrin hydrogel, prior to dehydration, is typically at least 0.0015%, 0.0020%, or 0.0030% wt.-% and typically no greater than 0.5 wt.-%.

In some embodiments, the salt comprises sodium citrate (i.e. trisodium citrate $Na_3C_6H_5O_7$). Commercially available fibrinogen can contain sodium citrate. The amount of sodium citrate can be at least 1, 2, 3, 4, or 5 wt.-% solids ranging up to 10, 11, 12, 13, 14 or 15 wt.-% solids. Commercially available fibrinogen can also contain sodium chloride. The amount of sodium chloride can be at least 1, 2, 3, 4, or 5 wt.-% solids ranging up to 10, 11, 12, 13, 14, or 15 wt.-% solids.

In some embodiments, a buffering agent is also present to maintain the desired pH range. In some embodiments, the pH ranges from 6 to 8 or 7 to 8 during the formation of the fibrin. Various buffering agent are known. Buffering agents are typically weak acids or weak bases. One suitable buffering agent is a zwitterionic compound known as HEPES (4-(2-hydroxyethyl)-1-piperazineethanesulfonic acid). Other buffering agents, such as those commonly known as Good buffers can also be utilized. In some embodiments, the buffering agent does not substantially contribute to the formation of the fibrin hydrogel. For example when the salt contains sodium and calcium chloride, the buffering agent HEPES does not substantially contribute to the formation of the fibrin hydrogel. This means that a fibrin hydrogel can be formed with the sodium and calcium salts in the absence of HEPES. Thus the concentration of HEPES in this example, as well as any other salt that does not substantially contribute to the formation of the fibrin hydrogel, is not included in the threshold concentration to form a fibrin hydrogel. However, HEPES as well as any other salt that does not substantially contribute to the formation of the fibrin hydrogel can contribute to the total salt concentration of the dehydrated fibrin hydrogel or fibrin composition in the event such salts are present after reducing the salt concentration, such as by rinsing.

As depicted in Table 1, of the forthcoming examples when the fibrin hydrogel salt (e.g. $NaCl+CaCl_2$) concentration was 0.423 wt.-% of the aqueous solution a fibrin hydrogel could not be formed from fibrinogen and thrombin. Without intending to be bound by theory, it is believed that a salt (e.g. $NaCl+CaCl_2$) concentration of 0.423 wt.-% is insufficient to solubilize the fibrinogen. However, when the concentration of salt was greater than 0.423 wt.-% a fibrin hydrogel readily formed. Hence, the threshold concentration to form a fibrin hydrogel is greater than 0.423 wt.-%. The threshold concentration of salt to form a gel is at least 0.430 wt.-% or 0.440 wt.-%, and in some embodiments at least 0.450, 0.500, 0.550, 0.600, 0.650, 0.700, 0.750, 0.800, 0.850, or 0.900 wt.-% of the aqueous solution. It is appreciated that the threshold concentration may vary to some extent depending on the selection of salt(s). In one embodiment, the salt concentration (e.g. $NaCl+Na_3C_6H_5O_7$) is 1.1 wt.-%. However, such salt concentration may be greater than the threshold concentration. The concentration of salt in the (i.e. initially formed) hydrogel is the same as the concentration of salt in the aqueous solution.

When a fibrin hydrogel is formed using a threshold concentration of salt and the hydrogel is dehydrated, the resulting dehydrated fibrin hydrogel has an even greater concentration of salt. For example as depicted in Table 1 of the forthcoming examples, the fibrin hydrogel forming salt (e.g. $NaCl+CaCl_2$) concentration is greater than 10, 15, 20, 25, or 30 wt.-%. As described in further detail in the forthcoming examples, high salt concentrations can cause (e.g. dermal) tissue irritation and damage during the healing process as indicated by inflammatory cell infiltration as well as collagen degeneration and mineralization.

The present method of preparing a fibrin composition comprises forming a fibrin hydrogel from an aqueous composition as previously described, and reducing the salt concentration below the threshold salt concentration to form a fibrin hydrogel. For embodiments wherein the (e.g. dehydrated) fibrin hydrogel is utilized for wound healing, the method comprises reducing the salt concentration below the concentration that can cause (e.g. dermal) tissue irritation and damage during the healing process.

In typical embodiments, the step of reducing the salt concentration comprises rinsing the fibrin hydrogel alone or in combination with a carrier material with a solution capable of dissolving the salt. The solution is typically aqueous comprising at least 50, 55, 60, 65, 70, 75, 80, 85, 90, or 95 wt.-%, or greater by volume water. The rinsing solution may further contain other water miscible liquids such as plasticizers. The fibrin hydrogel is typically rinsed with a volume of solution at least 1, 2, 3, 4, 5, 6, 7, 8, 9, or 10 times greater than the volume of the hydrogel. To reduce the salt concentration even further, the fibrin hydrogel may be rinsed with a volume of solution 11, 12, 13, 14, 15, 16, 17, 18, 19, or 20 times greater than the volume of the hydrogel. Another way of reducing the salt includes reacting the cation and/or anion of the salt, or in other words complexing the salt, such that the salt no longer forms ions in an aqueous solution such as bodily fluids of wounds. Another way of reducing the salt concentration is diluting with fibrin hydrogel plasticizer and/or by the addition of a carrier material. Further, various combination of these methods can be used.

The amount of fibrin hydrogel forming salt (e.g. $NaCl+CaCl_2$) removed from the fibrin hydrogel alone or in combination with a carrier material can depend on the amount of salt in the aqueous (e.g. starting) solution and thus, the amount of salt in the initially formed hydrogel. For example, when the aqueous (e.g. starting) solution comprises about 0.9 wt.-% salt, at least about 35 wt.-% of the salt is removed from the fibrin hydrogel. However, when the aqueous (e.g. starting) solution comprises about 1.25 wt.-% salt, greater than 50% of the salt is removed from the fibrin hydrogel. In some embodiments, at least 40%, 45%, 50%, 55%, 60%, 65%, 70%, 75%, 80%, 85% or 90% of the salt is removed from the hydrogel. In other embodiments, at least 91, 92, 93, 94, 95, 96, 97, 98, or 99% of the salt is removed from the hydrogel. If the threshold concentration is less than 0.9 wt-%, the amount of salt removed can be less than 35 wt.-%. In such embodiment, at least 5%, 10%, 15%, 20%, 25%, 30%, 35%, 40%, or 45% of the salt is removed from the hydrogel.

The fibrin hydrogel alone or in combination with a carrier material having the reduced fibrin hydrogel forming salt content is then dehydrated using any number of methods. This step may be referred to as dehydrating, drying or desiccating the hydrogel, all of which refer herein to the process of removing water content from the hydrogel as possible. Dehydration can therefore be accomplished using heat, vacuum, lyophilization, desiccation, filtration, air-drying, and the like. In some embodiments, the dehydrating is accomplished by freeze-drying, oven drying, a low pressure nitrogen steam, or a combination thereof. In some embodiments, lyophilization may be preferred since the resulting fibrin material is less likely to swell once in contact with an aqueous solution. However, the oven-dried fibrin gel sheets were observed to be more transparent and more uniform than the lyophilized sheets. The dehydration step may occur over a range of time, depending on the particular method used and the volume of the hydrogel. For example, the step may last for a few minutes, a few hours, or a few days. The present disclosure is not intended to be limited in this regard.

The dehydrated fibrin hydrogel as well as the fibrin composition further comprising the carrier material generally has a (e.g. hydrogel forming) salt concentration less than 30 wt.-% or 25 wt.-% (e.g. for a water content of zero ranging up to no greater than 20 wt.-%). When the dehydrated fibrin hydrogel as well as the fibrin composition is intended for use for wound healing the salt concentration is less than 20, 19, 18, 17, 16, 15, 14, 13, 12, 11, 10, 9, 8, 7, 6, 5, 4, 3, 2, or 1 wt.-% (e.g. for a water content of zero ranging up to no greater than 20 wt.-%). In some embodiments, the dehydrated hydrogel as well as the fibrin composition has a water content no greater than 19, 18, 17, 16, 15, 14, 13, 12, 11, 10, 9, 8, 7, 6, 5, 4, 3, 2, or 1 wt.-% or less. In some embodiments, the total salt concentration including the buffering salts are also within the concentration ranges just described. In some embodiments, the dehydrated hydrogel will swell when combined with water (i.e. rehydrated).

The salt concentration of the dehydrated hydrogel alone or in combination with a carrier material can be calculated when the kinds and amounts of salt utilized to prepare the fibrin hydrogel are known and the salt has not been removed, such as by rinsing with an aqueous solution. The (e.g. dehydrated) hydrogel, as well as the fibrin composition further comprising the carrier material, having a reduced salt concentration can be determine by measuring the conductivity of an aqueous solution containing a specified amount (1% w/w) using a suitable instrument such as a VWR Symphony B30PCI Benctop Multi Parameter Meter—pH, Conductivity, ISE. Quantitative and qualitative analysis of salt can be conducted using ion chromatography, as well as other techniques.

The dehydrated fibrin hydrogel typically has a water content of at least 1, 2, 3, 4, or 5 wt.-%. In some embodiments, the dehydrated fibrin hydrogel has a water content of at least about 10, 15, or 20 wt.-%. In other embodiments, the water content is no greater than 10 wt.-%.

The fibrin hydrogel alone or in combination with a carrier material is dehydrated to reduce the water content and thereby increase the fibrin concentration. Higher fibrin concentrations generally promote healing more rapidly than lower fibrin concentrations. The fibrin hydrogel, prior to dehydration typically comprises about 0.5 wt.-% to 5, 6, 7, 8, 9, 10, 11, 12, 13, 14, or 15 wt.-% fibrin. After dehydration, the fibrin composition typically comprises at least 10, 15, 20, 25, 30, 35, 40, 45, or 50 wt.-% fibrin. The fibrin concentration of the dehydrated fibrin hydrogel composition is typically no greater than 99 wt.-% and in some embodiments no greater than 95, 90, 85, or 80 wt.-%.

Since only a small concentration of fibrin-forming enzyme (e.g. thrombin) is needed to form fibrin and excess fibrin-forming enzyme (e.g. thrombin) is removed during rinsing, the concentration of fibrin-forming enzyme (e.g. thrombin) is also low in the dehydrated fibrin hydrogel as well as the fibrin composition further comprising the carrier material. The dehydrated fibrin hydrogel as well as the fibrin composition typically includes fibrin-forming enzyme (e.g. thrombin) in an amount of thrombin no greater than 0.05 U/mg, or 0.005 U/mg, or 0.0005 U/mg, or 0.00005 U/mg. In some embodiments, the amount of fibrin-forming enzyme (e.g. thrombin) is 1 or 0.1 ppm relative to the concentration of fibrin.

The (e.g. dehydrated) fibrin hydrogel as well as the fibrin composition further comprising the carrier material may include an amount of fibrinogen in a range from 0.1 wt.-% to 10 or 15 wt.-% relative to a total weight of the (e.g. dehydrated) fibrin hydrogel, or any amount within that range. In some embodiments, the (e.g. dehydrated) fibrin hydrogel as well as the fibrin composition includes fibrinogen in an amount no greater than 5, 4, 3, 2, 1, 0.1 or 0.05 wt.-%, relative to a total weight of the (e.g. dehydrated) fibrin hydrogel. When the conversion of fibrinogen to fibrin is 100%, the dehydrated fibrin hydrogel as well as the fibrin composition is substantially free of fibrinogen.

In some embodiments, the fibrin hydrogel as well as the fibrin composition further comprising the carrier material further comprises a plasticizer. Various water-miscible plasticizers are suitable for hydrogels. Such plasticizers typically comprise hydroxyl groups. Suitable plasticizers include for example $C_3$-$C_{24}$ sugar alcohols such as glycerol, diglycerol, triglycerol, xylitol, and mannitol as well as $C_3$-$C_{24}$ alkane diols such as butane diol and propane diol. In some embodiments, the plasticizer comprises an alkylene group having no greater than 12 carbons atoms. The (e.g. dehydrated) fibrin hydrogel may contain a single plasticizer or combination of plasticizers. When plasticizer is present, the concentration typically ranges from 0.5 wt.-% to 2 wt.-% of the aqueous starting precusor solution. The dehydrated hydrogel as well as the fibrin composition may comprise at least 5, 10, 15 or 20 wt.-% and typically no greater than 80, 70, 60, 50, or 40 wt-% plasticizer.

Inclusion of a plasticizer can result in a flexible dehydrated fibrin hydrogel composition, the properties of which can be determined by standard tensile and elongation testing. The film of flexible dehydrated hydrogel for testing can have a thickness of at least 10, 15 or 20 microns and typically no greater than 2 mm, 1 mm, 500 microns, or 250 microns. In some embodiments, the thickness is no greater than 200, 150, 100, 75, or 60 microns. The elongation can range from 10, 15, or 20% to 1000%. In some embodiments, the elongation (e.g. of a 50 micron film) is at least 50% or 75% and no greater than 200%, 150%, or 100%. The ultimate tensile strength is typically at least 0.1, 0.2, or 0.3 MPa and is typically no greater than 150 MPa. In some embodiments, the ultimate tensile strength (e.g. of a 50 micron film) is no greater than 50, 25, 10, or 5 MPa. The Young's elastic modulus is typically at least 0.5, 0.6, 0.7, 0.8, 0.9 or 1 MPa and is typically no greater than about 2000 MPa. In some embodiments, the Young's elastic modulus (e.g. of a 50 micron film) is at least 2 or 3 MPa and typically no greater than 100, 75 or 50 Mpa. Inclusion of the carrier material, especially those containing polymer(s), can also provide fibrin films having the tensile and elongation properties just described.

The (e.g. dehydrated) fibrin hydrogel as well as the fibrin composition further comprising the carrier material can include various additives, provided the additives do not detract from forming the fibrin hydrogel and reducing the salt concentration therefrom. Examples of additives can include any of antimicrobial agents, anti-inflammatory agents, topical anesthetics (e.g., lidocaine), other drugs, growth factors, polysaccharides, glycosaminoglycans. If an additive is included, it should be included at a level that does not interfere with the activity of the fibrin containing layer with respect to promoting healing of the wound.

Antimicrobial agents are agents that inhibit the growth of or kill microbes such as bacteria, mycobacteria, viruses, fungi, and parasites. Anti-microbial agents therefore include anti-bacterial agents, anti-mycobacterial agents, anti-viral agents, anti-fungal agents, and anti-parasite agents. Fibrin containing layers so loaded can be used to prevent or control infection.

Anti-inflammatory agents are agents that reduce or eliminate inflammation. Examples include alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclopofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, and zomepirac sodium.

The (e.g. dehydrated) fibrin hydrogel as well as the fibrin composition further comprising the carrier material can have various physical forms. In some embodiments, the fibrin hydrogel as well as the fibrin composition is formed prior to reducing the salt content. The fibrin hydrogel as well as the fibrin composition is typically sufficiently flowable at a temperature ranging from 0° C. to 37° C. such that the fibrin hydrogel takes the physical form of the container surrounding the fibrin hydrogel. For, example if the fibrin hydrogel as well as the fibrin composition is cast into a rectangular pan, the fibrin hydrogel as well as the fibrin composition forms into a sheet. Thus, the fibrin hydrogel as well as the fibrin composition can be cast into various shaped containers or in other words molded to provide (e.g. dehydrated) hydrogel of various shapes and sizes.

In one embodiment, the (e.g. dehydrated) fibrin hydrogel as well as the fibrin composition further comprising the carrier material may be provided as a fibrin foam. This can be accomplished by aerating the fibrinogen solution prior to addition of thrombin or aerating the fibrin hydrogel early in the polymerization process. After formation of the fibrin foam, salts can then be removed as previously described.

In another embodiment, the (e.g. dehydrated) fibrin hydrogel may be provided as particles. For example, (e.g. dehydrated) fibrin hydrogel microbeads may be formed, such as by the method described in U.S. Pat. No. 6,552,172 (Marx et al.). In yet another example, (e.g. dehydrated) fibrin hydrogel particles may be utilized as microcarriers such as described in US 2010/0291219 (Karp et al.). The salt content of the microbeads and microcarriers is reduced below the threshold concentration to form a fibrin hydrogel as previously described. The microbeads and microcarriers can further comprise carrier material as described herein.

In other embodiments, the dehydrated fibrin hydrogel as well as the fibrin composition further comprising the carrier material can be formed after reducing the salt content. For example, a sheet of (e.g. dehydrated) fibrin hydrogel or fibrin composition can be (e.g. laser or die) cut into pieces having various shapes and sizes. In another example, the dehydrated hydrogel or fibrin composition may be ground, pulverized, milled, crushed, granulated, pounded, and the like, to produce fibrin powder as described in WO2014/209620. In this embodiment, methods used for making (e.g. dehydrated) fibrin hydrogel particles are typically not dependent on oil-in-water emulsions.

When (e.g. dehydrated) fibrin hydrogel or fibrin composition further comprising a carrier material particles are formed into particles, the method may further involve size separating the particles. This may be accomplished most easily by sieving the particle composition through one or more appropriate sieves or filters having desired pore sizes. In some embodiments the particles can be sieved to arrive at populations having average diameters in the range of about 85-180, 90-170, 100-160, 100-150, 110-150, 120-140, or about 130 micrometers in average diameter. The fibrin particles further comprising a carrier material may be equal to or less than 80, 90, 100, 110, 120, 130, 140, 150, 160, 170, or 180 micrometers, provided they have a minimum average diameter of at least 10, 20, 30, 40 or 50 micrometers. It is to be understood that these average diameters refer to the diameter of the dehydrated particles rather than their rehydrated diameters. The particle volume may increase 10-250% of the initial volume after rehydration.

In some embodiments, (e.g. dehydrated) fibrin hydrogel or fibrin composition particles can be size restricted. In some aspects, the composition comprises a plurality of fibrin or fibrin composition particles, wherein at least 50% of which have an average diameter of 85-180 micrometers prior to hydration. In some embodiments, at least 55%, at least 60%, at least 65%, at least 70%, at least 75%, at least 80%, at least 85%, at least 90%, at least 95%, or more of the fibrin or fibrin composition particles have an average diameter of 85-180 micrometers.

The (e.g. dehydrated) fibrin hydrogel or fibrin composition particles may have spherical shape or an irregular non-spherical shape and size. The diameter of a non-spherical particle can be determined by summing its longest and its shortest dimension and dividing that sum by two. This is referred to as the average diameter of a single particle. Average diameter of a population of particles may be deduced based on a sieving analysis (i.e., the sieving analysis would provide a range of average diameters based on retention and/or flow through of particles). It will be understood that the term "average diameter" of a population of particles, defined as "summing its longest and its shortest dimension and dividing that sum by two", is conceptually similar to the term "average particle size", which refers to the "largest dimension" of the particles in a population of the particles.

In some embodiments, (e.g. dehydrated) fibrin hydrogel or fibrin composition particles are provided that are defined by their surface topology, topography, or roughness. The surface topology or roughness may be expressed in terms of the number and/or size of features (or protrusions) on the surface of the particles. Roughness can be observed using techniques commonly used in the art including optical profilometry and atomic force microscopy. The number of features on these particles may range from 2-100 typically. The size of these features (or protrusions) may be expressed in terms of absolute length or in terms of the ratio of the size of the feature (or protrusion) and the average diameter of the particles. In some embodiments, the size of the feature is about 1 micrometer, about 2 micrometers, about 3 micrometers, about 4 micrometers, about 5 micrometers, about 6 micrometers, about 7 micrometers, about 8 micrometers, about 9 micrometers, about 10 micrometers, or more. In other embodiments, the size of the feature is more than 10 micrometers, more than 15 micrometers, more than 20 micrometers, more than 25 micrometers, more than 30 micrometers, more than 35 micrometers, more than 40 micrometers, more than 45 micrometers, more than 50 micrometers, or more. In still other embodiments, the size is 10-100 micrometers. In other embodiments, the size is 1-10 micrometers. The ratio of feature size and particle average diameter may be about 5%, 10%, 15%, 20%, 25%, 30%, 35%, 40%, 45%, or 50%, or more. This surface roughness is important since it has been found that cells such as connective tissue progenitor cells are better able to bind to particles having a greater degree of surface roughness.

In some embodiments, the (e.g. dehydrated) fibrin hydrogel or fibrin composition particles have an average particle size in a range of 0.1 microns up to 100 microns. The fibrin particles can have an average particle size, of at least 0.1, 1, 2, 5, or 10 microns. The average particle is typically no greater than 1000 micrometers, 500, 200 or 100 microns.

The (e.g. dehydrated) fibrin composition described herein may be utilized in the treatment of a wound.

To facilitate delivery of the fibrin composition, the fibrin composition (e.g. particles) may be incorporated into a suitable carrier material to form various fibrin-containing gels, pastes, lotions, creams, and ointments. In another embodiment, (e.g. dehydrated) fibrin hydrogel particles can be dispersed in a (e.g. aqueous) liquid carrier material (e.g. an emulsion) to form a fibrin-containing spray.

The carrier material may be a solid, a liquid, or a mixture of solids and liquids. In some embodiments, the carrier material is not solely water, fibrin hydrogel plasticizer, or a combination thereof.

However, the carrier material may further comprise water and/or fibrin hydrogel plasticizer in combination with another carrier material, such as a polymer.

In typical embodiments, the carrier material may be characterized as physiologically inert, nonionic, and pH stable.

In some embodiments, the carrier material is water soluble. The carrier material may function as a thickener.

The carrier material, particularly in the case of water soluble polymers, such as polyvinyl N-vinyl lactam polymer, can be characterized by their Fikentscher K-value as described in Molyneaux, Water-Soluble Polymers: Properties and Behavior, Vol. 1, CRC Press, 1983, pp. 151-152. In some embodiments, the carrier material can have a Fikentscher K-value of at least K-10, K-15, K20, K-25, K-30, or K35. The Fikentscher K-value of commercially available water soluble polymers typically does not exceed K-120. In some embodiments, the Fikentscher K-value of the carrier material is at least K-40, K-50, K60, K70, K80, or K90.

The carrier material, particularly in the case of polymers, may also be characterized by molecular weight (Mw). In some embodiments, the carrier material has a molecular weight of at least 2,500; 5,000; 10,000; 25,000; or 50,000 g/mole. The molecular weight of the carrier material can range up to 1.5 or 2 million g/mole. In some embodiments, the molecular weight of the carrier material is at least 100,000; 250,000; or 500,000 g/mole.

The K value and molecular weight of the (e.g. polymeric) carrier material can even be higher than the ranges described. For example, the (e.g. polymeric) carrier material can be highly crosslinked such that it is no longer soluble in water at 25° C.

The carrier material, particularly in the case of polymers, may also be characterized by glass transition temperature. In some embodiments, the carrier material has a Tg of at least 120, 125, or 130° C. The Tg of the (e.g. polymeric) carrier material may range up to about 200° C. In some embodiments, the Tg of the carrier material is at least 140, 150, 160, 170, 180 or 190° C. However, the inclusion of swelling agents (e.g. carrier material plasticizer) can reduce the Tg of the carrier material. In this embodiment, the carrier material may have a Tg less than 25° C. or even less than 0° C.

In some embodiments, the carrier material is a film-forming polymer that forms a polymeric matrix. The (e.g. dehydrated) fibrin hydrogel may be interdispersed with the carrier material as discrete pieces or particles within the polymeric matrix of the carrier material. Alternatively, the carrier material may be interdispersed with the (e.g. dehydrated) fibrin hydrogel as discrete pieces or particles within a polymeric matrix of the (e.g. dehydrated) fibrin hydrogel. In other embodiments, the carrier material (e.g. polymer) and the (e.g. dehydrated) fibrin hydrogel are interdispersed within a common plasticizer.

In some embodiments, (e.g. dehydrated) fibrin particles can be admixed with natural or chemically modified and synthetic biological carrier materials such as collagen, keratin, gelatin, carbohydrates, and cellulose derivatives. Synthetic biological carrier materials can also be utilized such as described in previously cited US 2010/0291219 (Karp et al.).

In some embodiments, the biological carrier material comprises a bioerodible hydrogel such as polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In other embodiments, the biological carrier material is a biodegradable synthetic polymer such as polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polymers of lactic acid and glycolic acid, polyanhydrides, poly(ortho)esters, polyurethanes, poly(butic acid), poly(valeric acid), and poly(lactide-cocaprolactone) and polyvinylpyrrolidone.

In some embodiments, the biological carrier material comprises an uncrosslinked or crosslinked N-vinyl lactam polymer. Such polymer comprises polymerized units of N-vinyl lactam monomers. Nonlimiting examples of N-vinyl lactam monomers include for example N-vinyl-2-pyrrolidone; N-vinyl-2-valerolactam; N-vinyl-2-caprolactam; and mixtures of any of the foregoing. In some embodiments, the N-vinyl lactam monomer is N-vinyl-2-pyrrolidone. In some embodiments, the poly(N-vinyl lactam) polymer is a homopolymer of N-vinyl-2-pyrrolidone.

In other embodiments, the biological carrier material is a copolymer of N-vinyl lactam. Such copolymers further comprise polymerized units of at least one comonomer. Nonlimiting examples of comonomers include for example N,N-dimethylacrylamide, acrylic acid, methacrylic acid, hydroxyethylmethacrylate, acrylamide, 2-acrylamido-2-methyl-1-propane sulfonic acid or its salt, and vinyl acetate. A single comonomer or combination of comonomers can be employed.

In typical embodiments, the N-vinyl lactam copolymer comprises at least 50, 60, 70, 80, or 90 weight percent of polymerized units of N-vinyl lactam (e.g. N-vinyl-2-pyrrolidone) monomer(s). The N-vinyl lactam copolymer further comprises at least 10, 20, 30, 40, or 50 weight percent of polymerized units of comonomer(s).

Noncrosslinked N-vinyl lactam homopolymer and N-vinyl pyrrolidone/vinyl acetate copolymers are commercially available. Nonlimiting sources of commercially available poly(N-vinyl pyrrolidone) include Aldrich Chemical Co. of Milwaukee, Wis., BASF of Parsippany, N.J., ISP (GAF) of Wayne, N.J., Dan River Corporation of Danville, Va., Spectrum Chemical Manufacturing Corporation of Gardena, Calif, as well as Ashland Inc, Covington, KY as "Plasdone™ povidone".

In some embodiments, the (e.g. biological) carrier material comprises a crosslinked polymer. The crosslinked polymer may be any of the previously described natural or synthetic polymers wherein such polymer has been crosslinked. Crosslinking increase the molecular weight and K-value as previously described.

In some embodiments, the crosslinked polymer is a crosslinked synthetic polymer, such as crosslinked poly(N-vinyl lactam). In some embodiments, the (e.g. poly(N-vinyl lactam)) polymer is radiation-crosslinked (i.e. crosslinked by exposure to actinic radiation). The (e.g. poly(N-vinyl lactam)) polymer is typically crosslinked while the polymer in a solid form. In other embodiments, the (e.g. poly (N-vinyl lactam)) synthetic polymer is crosslinked by free-radical polymerization, either in bulk or in solution, of a precursor containing (e.g. N-vinyl lactam) monomer, optionally other monomers, and a crosslinking compound. (See for example, U.S. Pat. No. 4,931,282; incorporated herein by reference.)

The polymer of the solid carrier material can be provided in any form. Non-limiting examples of solid forms include particles, pellets, sheets, flakes, and bulk objects of various shapes, and coated objects of various shapes. For example U.S. Pat. Nos. 4,931,282; 5,225,473; and 5,389,376, incorporated herein by reference describe solid forms of poly(N-vinyl lactam. Typically, the crosslinked (e.g. poly(N-vinyl lactam)) polymer is in the form of particles having an average particle size (as can be determined by microscopy) of less than about 1, 0.5, 0.25 cm. In some embodiments, the average particle size is less than 1000, 750, or 500 microns. The average particle is typically at about 0.1, 0.5, 1, 2, 3, 4, 5, 6, 7, 8, 9, or 10 microns. In some embodiments, the average particle size is at least 25, 50, 75 or 100 microns. In some embodiments, the average particle size can be reduced during mixing. Alternatively, the polymer of the carrier material can be provided in a liquid form such as (e.g. an aqueous or organic-solvent based) solution, emulsion, or dispersion.

The carrier material can further comprise a swelling agent that can swell the (e.g. gurar) natural or (e.g. poly(N-vinyl lactam) synthetic polymer of the carrier material. In some embodiments, the swelling agent also functions to plasticize the fibrin gel. In yet other embodiments, the swelling agent can swell a modifying polymer, also present in the biological carrier material. The swelling agent is biocompatible with human skin.

The polymer of the carrier material can have a Swelling Capacity in water of at least about 15, typically at least about 30, and often at least about 40 as described in U.S. Pat. No. 5,409,966; incorporated herein by reference.

Nonlimiting examples of swelling agents include monohydric alcohols (e.g., ethanol, isopropanol, n-propanol), polyhydric alcohols, (e.g., ethylene glycol, propylene glycol, di propylene glycol, polyethylene glycol (Molecular Weight between 200 and 600) and glycerin), ether alcohols (e.g., glycol ethers), glycerol, polyglycerols (e.g. diglycerin, triglycerol, polyglycerin-3, hexaglycerol and decaglycerol), sorbitol and polyhydric alcohol ethoxylates (e.g. sorbeth-6, sorbeth-30, glycereth-1 to glycereth-31) methoxides of polyethylene glycol (Methoxy PEG-2 to Methoxy PEG 100), methoxides of polyhydric alcohol ethoxylates (e.g. glycereth-7 methoxide), as well as any other (e.g. polyol) swelling agents that do not cause skin irritation or toxic reaction, and water. In some embodiments, the previously described fibrin hydrogel plasticizers are utilized as a swelling agent. Various mixtures of swelling agent can also be employed.

Non-volatile and/or volatile swelling agents may be used. Non-volatility for the swelling agent is desired not only at room or body temperatures but also at the elevated temperatures of processing which range from about 75° C. to about 250° C. When the swelling agent in non-volatile, less than ten percent (10%) of a given 50 ml volume in a 4 oz. jar having a 4 cm diameter circular opening, evaporates after exposure to a temperature of 75° C. for one hour.

The swelling agent may comprise a volatile swelling agent in combination with a non-volatile swelling agent, such as a mixture of glycerin or polyethylene glycol with water. In some embodiments, the carrier material may comprise solely non-volatile swelling agents such as, for example, glycerin or polyethylene glycol. In some embodiments, the carrier material may comprise solely volatile swelling agents such as water. When the carrier material comprises a swellable polymer in combination with bound water, the carrier material may be characterized as a second hydrogel.

The swelling agent is typically a liquid. In some embodiments, humectant—type solid swelling agents like sorbitol could be used in conjunction with a co-swelling agent in order to dissolve the humectant such that it remains in the liquid swelling agent. Other humectants that could also be employed as swelling agents or co-swelling agents include: 1,2,6-hexanetriol, acetamide mea, aluminum hydroxide, arginine pca, butoxypropanol, butylene glycol, dimethyl imidazolidinone, dimethylsilanol hyaluronate, dipotassium glycyrrhizate, erythritol, ethoxydiglycol, fructose, glutamine, gluconic acid, glucose, glucose glutamate, glucuronic acid, glutamic acid, glycogen, glycyrrhizic acid, heilmoor clay, hexacosyl glycol, histidine, hyaluronic acid, hydrogenated honey, hydrogenated starch, hydrolysate, hydrolyzed collagen, hydrolyzed elastin, hydrolyzed glycosaminoglycans, hydrolyzed keratin, hydrolyzed silk, hydrolyzed soy protein, hydrolyzed wheat protein, hydroxyethyl sorbitol, inositol, inositol hexa-pca, lactamide mea, lactic acid, lactitol, lactose, lysine pca, magnesium pca, maltitol, manganese pca, mannitol, mel (honey extract), menthyl pca, methyl gluceth-10, methyl gluceth-20, pca (pidolic acid), lactamide, polydextrose, polyglucuronic acid, polyglyceryl sorbitol, potassium pca, ppg-20 methyl glucose ether, ppg-38-buteth-37, saccharide isomerate, serica, silk amino acids, sodium carboxymethyl chitin, sodium lactate, sodium mannuronate methylsilanol, sodium pca, sodium pca methylsilanol, sodium polyglutamate, soluble collagen, sorbitol, sucrose, tea-lactate, tea-pca, trehalose, trilactin, urea, xylitol, *Zea mays*, zinc pca, and combinations thereof.

The carrier material may comprise a modifying polymer. In some embodiments, the modifying polymer is present to maintain and/or increase cohesiveness while reducing adhesiveness. When added with the swelling agent, the modifying polymer becomes solublized or suspended in the swelling agent. Typically, the modifying polymer will form a viscous solution or viscous gel when combined with the swelling agent in a ratio of modifying polymer to swelling agent of 1:9.

In some embodiments, the modifying polymer comprises a polysaccharide or derivative thereof, a (meth)acrylate or derivate thereof, or cellulose or a derivative thereof. Specific examples of modifying polymers include for example hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; and derivatives and combinations thereof.

The concentration of carrier material admixed or interdispersed with the fibrin hydrogel can vary depending on the selection of carrier material(s).

In some embodiments, such as prior to dehydration, the fibrin hydrogel is combined with a carrier material in an amount of at least 0.5 wt.-% ranging up to about 10 wt.-% of the composition. The carrier material may comprise one or more of the previously described natural or synthetic polymer(s). In some embodiments, the fibrin hydrogel comprises a (e.g. poly(N-vinyl lactam) crosslinked synthetic polymer, as a carrier material, in an amount of at least 0.5 or 1.0 wt.-% ranging up to about 4, 5, 6, 7, 8, 9, or 10 wt.-%. Higher concentrations may be used when the synthetic polymer is uncrosslinked. In some embodiments, the fibrin hydrogel further comprises a modifying polymer(s) in an amount of at least 0.001, 0.005, or 0.1 wt.-% ranging up to about 1, 1.5 or 2 wt.-%. The fibrin hydrogel may further comprise a fibrin hydrogel plasticizer and/or swelling agent for the polymer of the carrier material is an amount of at least 0.5 or 1 wt.-% ranging up to 5, 6, 7, 8, 9 or 10 wt.-%. The mixture of fibrin hydrogel and carrier may be dispersed in a liquid carrier. The liquid carrier typically comprises a water/alcohol mixture.

The fibrin hydrogel and carrier material can be combined with each other in any suitable manner, such as by mixing.

The mixture of fibrin hydrogel, carrier material, and liquid carrier can be coated onto a carrier layer, such as foam, using any suitable method including for example dip coating, forward and reverse roll coating, wire wound rod coating and die coating.

After application the liquid carrier, as well as at least a portion of bound water of the hydrogel, is typically removed by dehydration, as previously described.

The dehydrated fibrin hydrogel composition alone or in combination with the carrier material may contain little or no water. In some embodiments, the concentration of carrier material can be in the same range as prior to dehydration, as previously described. For example, if the composition initially comprises 2 wt.-% of carrier material and 50 wt.-% of the water is removed, the dehydrated composition contain twice as much, i.e. 4 wt.-%. In other embodiments, the dehydrated fibrin hydrogel composition may contain 10 wt.-% to 99 wt.-% of carrier material. However, as the concentration of fibrin increases, the concentration of carrier material decreases. Thus, in some embodiments, the carrier material is no greater than 95, 90, 85, 80, 75, 70, 65, 60, 55, 50, 45, 40, 35, 30, 25, 20, 15, 10, 5, or 1 wt.-%.

In some embodiments, the dehydrated fibrin hydrogel composition comprises a (e.g. poly(N-vinyl lactam) crosslinked synthetic polymer, as a carrier material, in an amount of at least 15, 20, 25, or 30 wt.-% and typically no greater than 90, 85, 80, 75, 70, 65, 60, 55, or 50 wt.-%. Higher concentration may be useful when the synthetic polymer is uncrosslinked. Likewise, in some embodiments, the concentration of modifying polymer(s) in the dehydrated fibrin hydrogel composition can be in the same range as previously described. In other embodiments, the dehydrated fibrin hydrogel may contain a concentration ranging from 2 wt.-% to 15 wt.-% of modifying polymer(s). Likewise, in some embodiments, the concentration of fibrin hydrogel plasticizer and/or swelling agent for the polymer of the dehydrated fibrin hydrogel composition can be in the same range as previously described. In other embodiments, the dehydrated fibrin hydrogel may range from 2 wt.-% to 15 wt.-% of fibrin hydrogel plasticizer and/or swelling agent for the polymer of the carrier material.

In some embodiments, a carrier material may function as a pressure sensitive adhesive composition suitable for adhering to a wound.

In yet another embodiment, fibrin particles as described herein can be admixed with various (e.g. acrylic or silicone) skin adhesives to form a fibrin-containing skin adhesives.

In typical embodiments, (e.g. dehydrated) fibrin hydrogel is provided on or within a carrier layer at a coating weight that is sufficient to provide the desired effect (e.g. promoting wound re-epithelialization). In some embodiments, the coating weight of the (e.g. dehydrated) fibrin hydrogel is typically at least 0.2, 0.5, 1, 2, 3, 4, or 5 milligram per $cm^2$ and typically no greater than 30, 35, 20, 25, 20, 15, 10 or 5 milligrams per $cm^2$.

The (e.g. dehydrated) fibrin hydrogel composition described herein may be utilized as a wound dressing article. The wound dressing article described herein comprises a (e.g. dehydrated) fibrin composition in a suitable physical form such as a sheet (i.e. film), foam sheet, or fibrin (e.g. particles) disposed on or within a carrier layer. Thus, the (e.g. dehydrated) fibrin hydrogel layer can be provided in various forms as a continuous or discontinuous layer.

In some embodiments, the (e.g. dehydrated) fibrin hydrogel composition is formed prior to combining the (e.g. dehydrated) fibrin hydrogel composition with a carrier material or carrier layer. In other embodiments, a carrier layer is combined with the aqueous solution comprising fibrinogen, fibrin-forming enzyme (e.g. thrombin), and fibrin hydrogel forming salt or the fibrin hydrogel prior to reducing the salt and/or dehydration. For example, a fibrous (e.g. woven or nonwoven) substrate may be placed in a rectangular pan prior to adding the fibrin hydrogel thereby forming a sheet of fibrin hydrogel having a fibrous scrim embedded within the hydrogel. FIGS. 1-10 as follow illustrative some typical wound dressings articles.

FIG. 1 illustrates an embodiment of a fibrin article, suitable for use as a wound dressing. The fibrin article includes a (e.g. flexible) sheet 130 comprising or consisting of the (e.g. dehydrated) fibrin gel composition.

Figure 2:
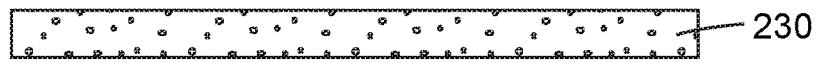
FIG. 2 is a schematic cross-section of an illustrative embodiment of a fibrin article suitable for a wound dressing comprising a fibrin composition in the form of a sheet of foam.

FIG. 2 illustrates another embodiment of a fibrin article, suitable for use as a wound dressing. The fibrin article includes a sheet of foam 230 comprising or consisting of the (e.g. dehydrated) fibrin gel composition. The foam may having various other shapes formed for example by molding the fibrin hydrogel composition (e.g. prior to hydrating) or cutting the foam into pieces after it is formed.

The fibrin sheet articles, such as illustrated in FIGS. 1 and 2 typically have a thickness of at least 10, 15 or 20 microns and typically no greater than 2 mm, 1 mm, 500 microns, or 250 microns. In some embodiments, the thickness is no greater than 200, 150, 100, 75, or 60 microns. The basis weight typically ranges from 2 to 10, 15, 20, 25 or 30 mg/cm$^2$.

The fibrin concentration of the sheet article is the same as the (e.g. dehydrated) fibrin hydrogel as previously described.

Figure 3:
FIG. 3 is a schematic cross-section of an illustrative embodiment fibrin article suitable for a wound dressing comprising a sheet of foam and fibrin particles.

FIG. 3 illustrates another embodiment of a fibrin article, suitable for use as a wound dressing. The fibrin article includes a carrier sheet of fibrin-containing foam 230 or foam lacking fibrin 310. The foam 230 or 310 further comprises a plurality of fibrin particles 332 comprising the (e.g. dehydrated) fibrin hydrogel disposed on and/or within the pores of the wound-facing surface of the foam. The particles may be fibrin microbeads, fibrin microcarriers, or fibrin powder as previously described.

Figure 4:
FIG. 4 is a schematic cross-section of an illustrative embodiment of a fibrin article suitable for a wound dressing comprising a fibrin-containing layer and a carrier layer.

Each of the embodiments of FIGS. 1-3 may further comprise a carrier layer disposed on a major surface of the fibrin-containing sheet article. A carrier layer is typically disposed on the opposing major surface as the wound-facing surface. For example, FIG. 4 illustrates an embodiment of a fibrin article, suitable for use as a wound dressing. The fibrin article includes a sheet 430 comprising or consisting of the (e.g. dehydrated) fibrin gel composition (e.g. 130, 230, or 310 together with 332) and a carrier layer 410.

In some embodiments, carrier layer 410 is a release liner. The release liner carrier may be disposed on the opposing major surface of both major surfaces (not shown) such that the fibrin-containing sheet is between the release liner layers.

Various release liners are known such as those made of (e.g. kraft) papers, polyolefin films such as polyethylene and polypropylene, or polyester. The films are preferably coated with release agents such as fluorochemicals or silicones. For example, U.S. Pat. No. 4,472,480 describes low surface energy perfluorochemical liners. Examples of commercially available silicone coated release papers are POLYSLIK™, silicone release papers available from Rexam Release (Bedford Park, Ill.) and silicone release papers supplied by LOPAREX (Willowbrook, Ill.). Other non-limiting examples of such release liners commercially available include siliconized polyethylene terephthalate films commercially available from H. P. Smith Co. and fluoropolymer coated polyester films commercially available from 3M under the brand "ScotchPak™" release liners.

In other embodiments, the carrier layer 410 may comprise a variety of other (e.g. flexible and/or conformable) materials such as polymeric films and foams as well as various nonwoven and woven fibrous materials, such as gauze. In some embodiments, the carrier layer is absorbent, such as an absorbent foam. In other embodiments, the carrier layer is non-absorbent, such as a polymeric film.

Figure 5:
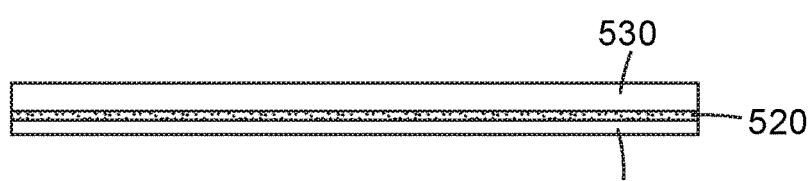
FIG. 5 is a schematic cross-section of an illustrative embodiment of a fibrin article suitable for a wound dressing comprising a fibrin-containing layer, a carrier layer, and a (e.g. pressure sensitive) adhesive.

In some embodiments, the fibrin article, suitable for use as a wound dressing, further comprises a (e.g. pressure sensitive) adhesive. The adhesive may be utilized to bond the fibrin composition (e.g. sheet or particles) to the carrier layer. For example, FIG. 5 illustrates a fibrin-containing sheet 530 comprising or consisting of the (e.g. dehydrated) fibrin gel composition and a carrier layer 510 such as a polymeric film or foam. A (e.g. pressure sensitive) adhesive layer 520 bonds the fibrin-containing sheet 530 to the carrier layer 510. Fibrin-containing sheet 530 may be 130, 230, or 310 together with 332 as previously described with reference to FIGS. 1-3.

Figure 6:
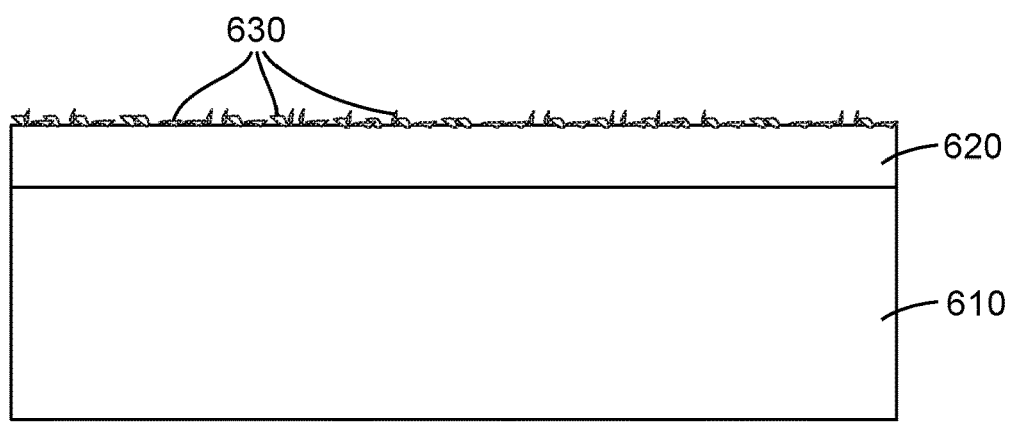
FIG. 6 is a schematic cross-section of an illustrative embodiment of a fibrin article suitable for a wound dressing comprising a carrier layer, a (e.g. pressure sensitive) adhesive; and (e.g. dehydrated) fibrin hydrogel containing particles.

In some embodiments, the fibrin article comprises a skin contacting adhesive for bonding the article to the skin (e.g. of a mammal such as a human). Such skin contact adhesive is typically a pressure sensitive adhesive. In some embodiments, the pressure sensitive adhesive may bond fibrin particles to a carrier layer. The fibrin particles and optionally portions of the pressure sensitive adhesive may contact the wound during use. For example, FIG. 6 illustrates another embodiment of a fibrin article, suitable for use as a wound dressing. The fibrin article includes a carrier layer 610 that may be a release liner, a polymeric film or foam, etc., a pressure sensitive adhesive layer 620 is disposed on the carrier layer 610 and fibrin particles 630, as described herein, are disposed on and optionally at least partially embedded in the pressure sensitive adhesive layer. The skin contact adhesive is typically covered by a removable release liner until use.

Figure 7:
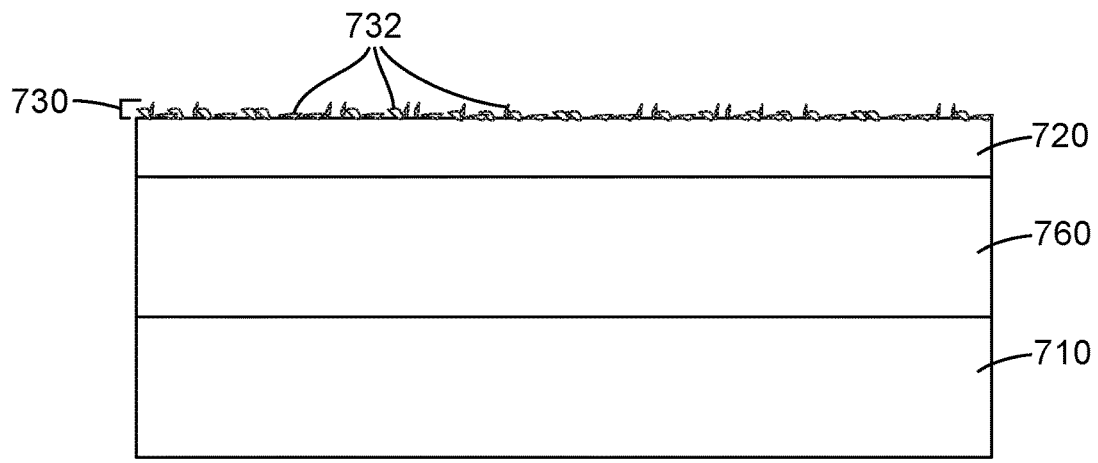
FIG. 7 is a schematic cross-section of an illustrative embodiment of a fibrin article suitable for a wound dressing comprising a carrier layer, an absorbent, a (e.g. pressure sensitive) adhesive; and fibrin-containing layer.

In some embodiments, the wound dressing comprises an absorbent layer. The absorbent layer is typically disposed between the wound facing fibrin-containing layer and a polymeric film. For example, FIG. 7 illustrates another embodiment of a fibrin article, suitable for use as a wound dressing. The fibrin article includes a carrier layer 710 that may be a (e.g. flexible) polymeric film. An absorbent layer 760 such as a polymeric foam is disposed on the carrier layer 710. A pressure sensitive adhesive ("PSA") layer 720 is disposed on the absorbent layer 760 and a fibrin-containing layer 730 is disposed on the pressure sensitive adhesive layer 720. The fibrin-containing layer may be any of the previously described fibrin-containing layers such as sheet 130, foam sheet 230, or fibrin particles 332.

Figure 8:
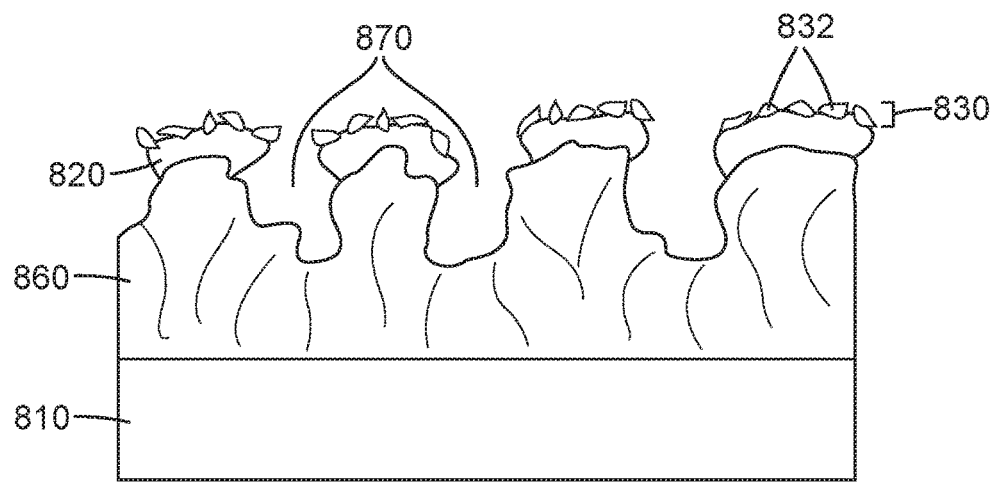
FIG. 8 is a schematic cross-section of an illustrative carrier layer and fibrin-containing layer comprising a discontinuous skin adhesive and (e.g. dehydrated) fibrin hydrogel containing particles.

As shown in FIG. 8, an adhesive layer 820 may be provided in a discontinuous form, at external surfaces of absorbent layer 860, to allow penetration of wound fluids and cellular debris into the absorbent foam layer. In some embodiments, the adhesive is a pressure sensitive adhesive. In other embodiments, the adhesive is not a pressure sensitive adhesive. The fibrin particles 832 in fibrin layer 830 are thus displayed in correspondingly discontinuous manner at the outer surface of absorbent layer 860. The adhesive layer 820 may extend into and through a portion of absorbent layer 860. Portions of the adhesive layer 820 can extend over open cells 870, although it is desirable at least a portion (e.g., at least 10%, or at least 50%) of the cells at the external surface of absorbent layer 860 are not closed with the adhesive. Absorbent layer 860 can be adhered to (e.g. flexible) film layer 810 by a suitable adhesive layer. In this embodiment, the fibrin particles may be fibrin microbeads, fibrin microcarriers, or fibrin powder as previously described. In one embodiment, a solution of pressure-sensitive adhesive can be sprayed onto a carrier layer such as an open cell foam at a suitable coating weight (e.g., 5-15 mg/cm$^2$) and after drying the PSA layer, fibrin particles can be coated onto the adhesive coated surface. The fibrin particles can thus be deposited on an exterior surface of the foam with some additional loading into pores of the open cell foam. Such a fibrin particles/PSA/absorbent foam construct has been observed to readily absorb moisture. This approach is also suitable for incorporating fibrin particles on elastomeric carrier layers.

In another embodiment, a fibrin particle layer can be disposed on a pressure-sensitive adhesive layer, which in turn is disposed on a flexible, porous, non-woven backing layer. The non-woven backing layer can be reinforced with filaments (e.g., polyester filaments) for added strength. An example of such a non-woven-backing coated with a (hypoallergenic) pressure-sensitive adhesive can include sterile skin closure strips (e.g., STERI-STRIPS, available from 3M Co., St. Paul, MN). The addition of a fibrin (e.g. particle) layer to such sterile skin closure strips can have beneficial effects, for example, in scar management at incision or wound sites (i.e., to reduce scar formation).

Figure 9:
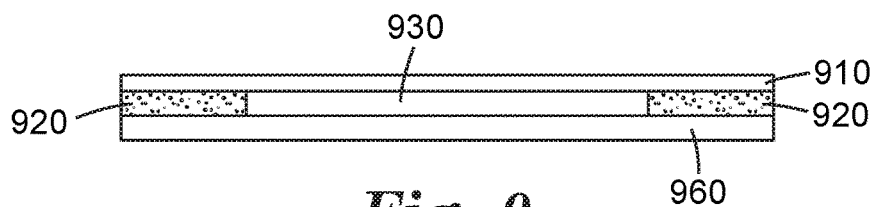
FIG. 9 is a schematic cross-section of another illustrative embodiment of a fibrin article suitable for a wound dressing comprising a carrier layer, fibrin-containing layer, skin contact pressure sensitive adhesive, and release liner.
Figure 10:
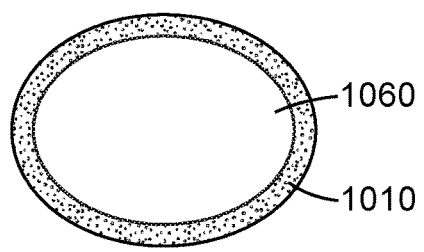
FIG. 10 is a top plan view of the wound-facing surface of the article of FIG. 10.
Figure 11:
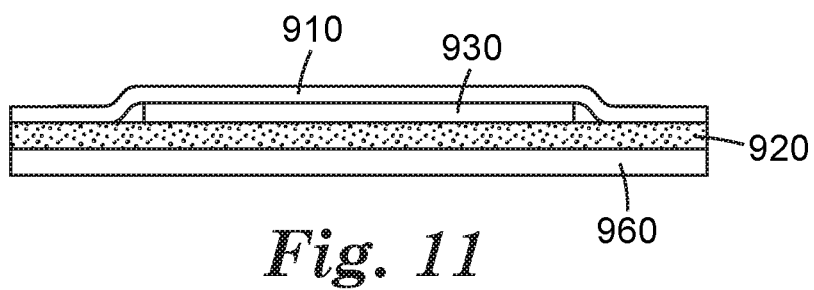
FIG. 11 is a schematic cross-section of another illustrative embodiment of a fibrin article suitable for a wound dressing comprising a carrier layer, fibrin-containing layer, skin contact pressure sensitive adhesive, and release liner.

In other embodiments, a skin contact adhesive is located at the periphery of the article such that the adhesive typically contacts the skin outside of the wound such as near the periphery of a wound. The skin contact adhesive is typically covered by a removable release liner until use. For example, FIG. 9 illustrates another embodiment of a fibrin article, suitable for use as a wound dressing. The fibrin article includes a carrier layer 960 that is typically a polymeric film, a pressure sensitive skin adhesive 920 is disposed at peripheral regions of the film, a fibrin sheet 930 is disposed on film 960 in the middle region between adhesive 920, a removable release liner 910 is disposed on the fibrin sheet and the adhesive. Alternatively, the release liner may be disposed only upon the adhesive as depicted in FIG. 10. In FIG. 11, the (e.g same) skin contact adhesive is utilized to bond the fibrin sheet to the polymeric film carrier layer 960.

In some embodiments, the carrier layer of the wound dressing is a flexible film layer, (also referred to as a "backing" layer), typically includes a liquid impervious, moisture vapor permeable (e.g. breatheable) polymeric film. The liquid impervious, moisture vapor permeable polymeric film is a conformable organic polymeric material that preferably retains its structural integrity in a moist environment. Herein, "conformable" films are those that conform to a surface, even upon movement of the surface, as with the surface of a body part. As such, when the flexible film layer is applied to an anatomical feature, it conforms to the surface even when the surface is moved. The preferred flexible film layer is also conformable to animal anatomical joints. When the joint is flexed and returned to its unflexed position, the flexible film layer stretches enough to accommodate the flexion of the joint, but is resilient enough to continue to conform to the joint when the joint is returned to its unflexed condition. A description of this characteristic of flexible film layers preferred for use in wound dressings of the present disclosure can be found, for example, in U.S. Pat. No. 5,088,483 (Heineke) and U.S. Pat. No. 5,160,315 (Heineke).

Suitable films have a composition and thickness that allow for the passage of moisture vapor through them. The film aids in the regulation of water vapor loss from the wound area beneath the dressing. The film also acts as a barrier to both bacteria and to liquid water or other liquids.

The moisture vapor permeable polymeric films for use as flexible film layers in the present disclosure can be of a wide range of thicknesses. In some embodiments, the flexible film layers have a thickness of at least 10 or 12 microns ranging up to 250 microns. In some embodiments, the flexible film layer has a thickness no greater than 75 microns.

Moisture vapor transmission rate ("MVTR") properties of a wound dressing article are important to allow the wound under the wound dressing to heal in moist conditions without causing the skin surrounding the wound to become macerated, and to facilitate optimum wear time and ease of removal.

A dry MVTR (or upright MVTR) of wound dressings or various components thereof, including the flexible film layer, can be measured by ASTM E-96-80 (American Society of Testing Materials) at 40° C. and 20% relative humidity using an upright cup method. Wet MVTR (or inverted MVTR) can be measured by the same method except that the sample jars are inverted so the water is in direct contact with the test sample.

In some embodiments, the film has a dry MVTR that is less than the wet MVTR of the film. For example, the film may have a dry MVTR of at least 300 $g/m^2/24$ hours and a wet MVTR of at least 500, 1000, 2000 or 3000 $g/m^2/24$ hours. In some embodiments, the film has a wet MVTR greater 10,000 $g/m^2/24$ hours or 15,000 $g/m^2/24$ hours.

Examples of suitable materials for the liquid-impervious, moisture-vapor permeable polymeric films of the flexible film layer include synthetic organic polymers including, but not limited to: polyurethanes commercially available from B.F. Goodrich, Cleveland, OH, under the trade designation ESTANE, including ESTANE 58237 and ESTANE 58245; polyetheramide block copolymers commercially available from Elf Atochem, Philadelphia, PA, under the trade designation PEBAX, including PEBAX MV 1074; polyetherester block copolymers commercially available from DuPont, Wilmington, DE, under the trade designation HYTREL; and thermoplastic elastomers commercially available from DSM Engineering Plastics, Evansville, IN, under the trade designation ARNITEL VT. The polymeric films can be made of one or more types of monomers (e.g., copolymers) or mixtures (e.g., blends) of polymers. Preferred materials are thermoplastic polymers, e.g., polymers that soften when exposed to heat and return to their original condition when cooled. A particularly preferred material is a thermoplastic polyurethane.

Flexible films of the wound dressing articles of the present disclosure can also include other breathable materials including, for example, nonwoven, woven, and knit webs, porous films (e.g., provided by perforations or microporous structure), foams, paper, or other known flexible films. A preferred flexible film includes a combination of a liquid-impervious, moisture-vapor permeable polymeric film and a moisture-vapor permeable nonwoven web that can, among other advantages, impart enhanced structural integrity and improved aesthetics to the dressings. These layers of film and web may or may not be coextensive. A preferred such nonwoven web is a melt processed polyurethane (such as that available under the trade designation MORTHANE PS-440 from Morton International, Seabrook, NH), or hydroentangled nonwoven polyester or rayon-polyester webs (such as those available under the trade designation SONTARA 8010 or SONTARA 8411 from DuPont, Wilmington, DE).

In some embodiments, flexible film layer is translucent, semi-transparent, or transparent, although this is not a requirement. Some examples of wound dressings that include a transparent or translucent flexible film layer are available under the trade designation TEGADERM, available from 3M Co., St. Paul, MN.

A low adhesion coating (low adhesion backsize or LAB) can be provided on the flexible film layer on the side that may come into contact with an optional support layer. The low adhesion coating reduces the need to change the dressing due to unwanted dressing removal when other tapes or devices are placed on the dressing and removed, and reduces the surface friction of the dressing on linen or other fabrics, thereby offering additional protection against the accidental removal of dressing. A description of a low adhesion coating material suitable for use with a wound dressing article of the present disclosure can be found in U.S. Pat. No. 5,531,855 (Heineke) and U.S. Pat. No. 6,264,976 (Heineke).

In some embodiments, the wound dressing comprises an absorbent layer. In some embodiments, the absorbent layer can include an absorbent foam layer, or at least a portion of an absorbent foam layer disposed on the flexible film layer. A suitable foam layer can include, for example, an open cell foam selected from among the open cell foams described in U.S. Pat. No. 6,548,727 (Swenson). Suitable open cell foams preferably have an average cell size (typically, the longest dimension of a cell, such as the diameter) of at least about 30 microns, more preferably at least about 50 microns, and preferably no greater than about 800 microns, more preferably no greater than about 500 microns, as measured by scanning electron microscopy (SEM) or light microscopy. Such open cell foams when used in wound dressings of the present disclosure allow transport of fluid and cellular debris into and within the foam. In some embodiments, the foam includes a synthetic polymer that is adapted to form a conformable open cell foam that absorbs wound exudate. Examples of suitable materials for the absorbent, substantially nonswellable foams include synthetic organic polymers including, but not limited to: polyurethanes, carboxylated butadiene-styrene rubbers, polyesters, and polyacrylates. The polymeric foams can be made of one or more types of monomers (e.g., copolymers) or mixtures (e.g., blends) of polymers. Preferred foam materials are polyurethanes. A particularly preferred foam is a polyurethane, available under the trade designation POLYCRIL 400 from Fulflex, Inc., Middleton, R.I. In other embodiments, the foam comprises or consists of the (e.g. dehydrated) fibrin hydrogel.

In another embodiment, the absorbent layer may comprise a non-woven or a fiber material. In an embodiment where the absorbent material includes a fiber material, the fiber material can be a sheath-core fiber having a central core of absorbent fiber and a sheath comprising pressure-sensitive adhesive.

In some embodiments, the absorbent layer may extend around a peripheral region of the wound dressing, to absorb fluids that might otherwise accumulate on skin and result in undesirable skin degradation (e.g., maceration). In such embodiments, an absorbent layer would not need to be included in a more central region of the wound dressing (e.g., the portion of the wound dressing that is in contact with the wound, or positioned over the wound).

The fibrin article, suitable for use as a wound dressing, may comprise various adhesives to bond layers of the article. The fibrin article may also comprises various PSAs for bonding the article to skin. The (e.g. PSA) adhesive layer can be continuous, discontinuous, pattern coated, or melt-blown, for example.

PSAs typically have a storage modulus (G') of less than $1 \times 10^6$ dynes/cm$^2$ at 25° C. and a frequency of 1 hertz. In some embodiments, the PSA has storage modulus (G') of less than 9, 8, 7, 6, 5, 4, or $3 \times 10^5$ dynes/cm$^2$ at 25° C. and a frequency of 1 hertz.

Examples of PSAs include rubber based adhesives (e.g., tackified natural rubbers, synthetic rubbers, and styrene block copolymers), acrylics (e.g., polymerized (meth)acrylates), poly(alpha-olefins), polyurethanes, and silicones. Amine containing polymers can also be used which have amine groups in the backbone, pendant thereof, or combinations thereof. A suitable example includes a poly(ethyleneimine).

Useful adhesives can be any of those that are compatible with skin and useful for wound dressings, such as those disclosed in U.S. Pat. Nos. Re. 24,906 (Ulrich), U.S. Pat. No. 5,849,325 (Heinecke et al.), and U.S. Pat. No. 4,871,812 (Lucast et. al.) (water-based and solvent-based adhesives); U.S. Pat. No. 4,833,179 (Young et al.) (hot-melt adhesives); U.S. Pat. No. 5,908,693 (Delgado et al.) (microsphere adhesives); U.S. Pat. Nos. 6,171,985 and 6,083,856 (both to Joseph et al.) (low trauma fibrous adhesives); and, U.S. Pat. No. 6,198,016 (Lucast et al.), U.S. Pat. No. 6,518,343 (Lucast et al.), and U.S. Pat. No. 6,441,082 (Gieselman) (wet-skin adhesives). Inclusion of medicaments or antimicrobial agents in the adhesive is also contemplated, as described in U.S. Pat. No. 4,310,509 (Berglund) and U.S. Pat. No. 4,323,557 (Rosso).

The adhesive can be coated on the carrier layer by a variety of processes, including, direct coating, lamination, and hot lamination. In some embodiments, the adhesive may be coated as a microstructured adhesive layer.

Silicone and acrylic based pressure sensitive adhesives are most commonly utilized for adhering to the skin, whereas the other classes of adhesives can be utilized to bond layers of the fibrin article suitable for use as a wound dressing.

Silicone PSAs include two major components, a polymer or gum, and a tackifying resin. The polymer is typically a high molecular weight polydimethylsiloxane or polydimethyldiphenyl-siloxane, that contains residual silanol functionality (SiOH) on the ends of the polymer chain, or a block copolymer including polydiorganosiloxane soft segments and urea terminated hard segments. The tackifying resin is generally a three-dimensional silicate structure that is end-capped with trimethylsiloxy groups (OSiMe$_3$) and also contains some residual silanol functionality. Examples of tackifying resins include SR 545, from General Electric Co., Silicone Resins Division, Waterford, NY, and MQD-32-2 from Shin-Etsu Silicones of America, Inc., Torrance, CA. Manufacture of typical silicone PSAs is described in U.S. Pat. No. 2,736,721 (Dexter). Manufacture of silicone urea block copolymer PSA is described in U.S. Pat. No. 5,214,119 (Leir et al.).

In some embodiments, the silicone adhesive may be characterized as gentle to skin such as descrived in US2011/0212325, US2011/0206924, US2011/0206923, US2013/0040073, U.S. Pat. Nos. 7,407,709 and 787,268.

In some embodiments, the PSAs is an acrylic PSAs typically having a glass transition temperature of about −20° C. or less and may include from 100 to 60 weight percent of a C4-C12 alkyl ester component such as, for example, various (meth)acrylate monomers including isooctyl acrylate, 2-ethyl-hexyl acrylate and n-butyl acrylate and from 0 to 40 weight percent of a polar component such as, for example, acrylic acid, methacrylic acid, ethylene, vinyl acetate, N-vinyl pyrrolidone and styrene macromer.

Suitable acidic monomers for preparing (meth)acrylic PSAs include those containing carboxylic acid functionality such as acrylic acid, methacrylic acid, itaconic acid, and the like; those containing sulfonic acid functionality such as 2-sulfoethyl methacrylate; and those containing phosphonic acid functionality. Preferred acidic monomers include acrylic acid and methacrylic acid.

Additional useful acidic monomers include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, B-carboxyethyl acrylate, 2-sulfoethyl methacrylate, styrene sulfonic acid, 2-acrylamido-2-methylpropane sulfonic acid, vinyl phosphonic acid, and the like, and mixtures thereof.

Due to their availability, acidic monomers of the present invention are typically the ethylenically unsaturated carboxylic acids. When even stronger acids are desired, acidic monomers include the ethylenically unsaturated sulfonic acids and ethylenically unsaturated phosphonic acids. Sulfonic and phosphonic acids generally provide a stronger interaction with a basic polymer. This stronger interaction can lead to greater improvements in cohesive strength, as well as higher temperature resistance and solvent resistance of the adhesive.

Suitable basic monomers for preparing (meth)acrylic PSAs include those containing amine functionality such as vinyl pyridine, N,N-diethylaminoethyl methacrylate, N,N-dimethylamino-ethyl methacrylate, N,N-diethylaminoethyl acrylate, N,N-dimethylaminoethyl acrylate, and N-t-butylaminoethyl methacrylate. Preferred basic monomers include N,N-dimethylaminoethyl methacrylate, and N,N-dimethylaminoethyl acrylate.

The (meth)acrylic PSAs may be self-tacky or tackified. Useful tackifiers for (meth)acrylics are rosin esters such as that available under the trade name FORAL 85 from Hercules, Inc., aromatic resins such as that available under the trade name PICCOTEX LC-55WK from Hercules, Inc., aliphatic resins such as that available under the trade name PICCOTAC 95 from Hercules, Inc., and terpene resins such as that available under the trade names PICCOLYTE A-115 and ZONAREZ B-100 from Arizona Chemical Co. Other materials can be added for special purposes, including hydrogenated butyl rubber, pigments, and curing agents to vulcanize the adhesive partially. Examples of acid-modified tackifiers include acid-modified polyhydric alcohol rosin ester tackifiers as described in U.S. Pat. No. 5,120,781 (Johnson).

In certain embodiments, the (e.g. acrylic) PSA comprises polymerized unit of a poly(alkylene oxide) such as poly(ethylene oxide) and/or poly(propylene oxide). The PSA typically comprises at least 5, 10 or 15 wt.-% and typically no greater than about 30 wt.-% of polymerized poly(alkylene oxide).

In some embodiments, a poly(alkylene oxide) copolymer is blended with a (meth)acrylic copolymer. Examples of useful poly(alkylene oxide) copolymers include, but are not limited to, those poly(alkylene oxide) copolymers available under the trade designations TETRONIC (tetrafunctional block copolymers derived from sequential addition of propylene oxide and ethylene oxide to ethylene diamine with hydrophilic endblocks) and TETRONIC R (tetrafunctional block copolymers derived from sequential addition of propylene oxide and ethylene oxide to ethylene diamine with hydrophobic endblocks) copolymers available from BASF, Mt. Olive, N.J.; PLURONIC (triblock copolymers with poly(ethylene oxide) end blocks and poly(propylene oxide) midblock) and PLURONIC R (triblock copolymers with poly(propylene oxide) endblocks and poly(ethylene oxide) midblock) copolymers available from BASF; UCON Fluids (random copolymers of ethylene oxide and propylene oxide) available from Union Carbide, Danbury, Conn. Various combinations of poly(alkylene oxide) copolymers can also be used. Preferred nonreactive hydrophilic polymer components are block copolymers of polyethylene glycol and propylene glycol available from BASF, Germany under the trade name PLURONIC.

In other embodiments, a poly(alkylene oxide) monomer having a copolymerizable (e.g. vinyl) group is included during the polymerization of the acrylic polymer. Commercially available monomers include 2-(2-ethoxyethoxy)ethyl acrylate which is available under the trade designation "SR-256" from Sartomer Company, West Chester, PA; the methoxy poly(ethylene oxide) acrylate which is available under the trade designation "No. 8816" from Monomer-Polymer & Dajac Laboratories, Inc., Trevose, PA; the methoxy poly(ethylene oxide) methacrylates of 200 Daltons, 400 Daltons, and 1000 Daltons which are available under the trade designations "No. 16664", "No. 16665" and "No. 16666", respectively, from Polysciences, Inc., Warrington, PA; and the hydroxy poly(ethylene oxide) methacrylate which is available under the trade designation "No. 16712" from Polysciences, Inc., Warrington, PA.

Examples of acrylic adhesive compositions include a 97:3 iso-octyl acrylate:acrylamide copolymer 65:15:20 2-ethylhexylacrylate:acrylic acid:copolymer blended with a nonreactive polyakylene oxide copolymer under the trade designation PLURONIC. Other suitable examples include a 90:10 iso-octyl acrylate:acrylic acid copolymer, a 70:15:15 isooctyl acrylate:ethylene oxide acrylate:acrylic acid terpolymer, and a 25:69:6 2-ethylhexylacrylate:butyl acrylate:acrylic acid terpolymer. Additional useful adhesives are described in U.S. Pat. Nos. 3,389,827, 4,112,213, 4,310,509, and 4,323,557.

Inclusion of medicaments or antimicrobial agents in the adhesive is also contemplated, as described in U.S. Pat. Nos. 4,310,509 and 4,323,557.

Pressure sensitive adhesives for wound dressings preferably transmit moisture vapor at a rate greater to or equal to that of human skin. While such a characteristic can be achieved through the selection of an appropriate adhesive, it is also contemplated in the present disclosure that other methods of achieving a high relative rate of moisture vapor transmission may be used, such as pattern coating the adhesive on the backing, as described in U.S. Pat. No. 4,595,001 (Potter et al.).

A composite of flexible film layer coated with pressure-sensitive adhesive layer preferably has a moisture vapor transmission rate of at least 300 g/m$^2$/24 hrs/37° C./100%-10% relative humidity ("RH"), more preferably at least 700 g/m$^2$/24 hrs/37° C./100%-10% RH, and even more preferably at least 2000 g/m$^2$/24 hrs/37° C./100%-10% RH using the inverted cup method as described in U.S. Pat. No. 4,595,001.

In some embodiment, the method of making a fibrin article generally comprises providing a (e.g. dehydrated) fibrin composition and disposing the fibrin composition on or within a carrier. In some embodiments, the carrier is a carrier layer such as a release liner, a polymeric film or foam, or a nonwoven or woven fibrous material. When the fibrin composition is in a particle form, the methods of making the wound dressing can include distributing fibrin particles onto a (e.g. pressure-sensitive) adhesive layer disposed on a carrier. Alternatively, the fibrin particles can be suspended in a liquid (e.g., an inert, volatile fluorinated liquid) and spray dried in a dehydrated form onto the surface of a (e.g. pressure-sensitive) adhesive layer disposed on a carrier layer. Examples of suitable wound dressings that include a pressure-sensitive adhesive layer disposed on flexible film layer include TEGADERM wound dressings (e.g., TEGADERM 1626) available from 3M Co., St. Paul, MN. In one embodiment, the fibrin-containing layer (e.g. sheet or particles) are applied to the surface of a pressure-sensitive adhesive layer of a TEGADERM wound dressing.

A wound dressing article of the present description is typically provided in a package format (i.e., positioned in a sealed package). The interior of the sealed package is typically sterile. Examples of wound dressing packages suitable for use with the wound dressings and methods of this disclosure include, for example, polymeric packages and foil packages. A wide variety of polymeric materials may be used to make non-porous packages suitable for use with the wound dressings. The packaging material may be, for example, polyethylene, polypropylene, copolymers of ethylene and propylene, polybutadiene, ethylene-vinyl acetate, ethylene-acrylic acid, or ionomeric films. Suitable foil packages can include aluminum foil packages. In some embodiments, the packaging material may be used as sheets of material which are placed above and below the wound dressing and then sealed on four sides to generate the package. In other embodiments, a pre-made pouch is utilized which has 3 sides already sealed. After the wound dressing article is placed within the pouch the fourth side is sealed to form the package. Sealing of the package can be achieved by heat sealing (i.e. by the application of heat and pressure to form a seal) or the use of adhesive sealants can be used to seal the packages (for example pressure sensitive adhesive sealants or cold seal sealants). Typically, heat sealing is used. Additionally, packaging systems can be used which include placing the wound dressing in a porous package that is then placed in a non-porous package, such as a foil package. The foil package prevents moisture loss prior to use and the porous package permits easy handling during use.

An advantage of a wound dressing article of the present disclosure is that it can be sterilized by a terminal sterilization process that includes exposure to ethylene oxide or, advantageously, gamma-irradiation. This irradiation can be carried out whether or not the wound dressing article is contained within a package. The exposure times and levels of radiation doses applied to the wound dressings to achieve sterilization can vary based upon a variety of factors, including the gamma equipment used as well as the inherent bioburden levels present in the wound dressing. Typically, to achieve sterilization of a wound dressing, a Sterility Assurance Level (SAL) of $10^{-6}$ is required. This SAL level is typically achieved by exposing the wound dressing to a minimum cumulative gamma irradiation dose. Depending on the bioburden levels in an unsterilized dressing and the size of the dressing, the minimum cumulative dose can range from about 10 kGy to about 35 kGy. Typically the minimum cumulative dose is about 15 to 30 kGy. In other embodiment, a dosage of about 50 to 60 kGy may be utilized. The required gamma radiation dose to achieve sterility can be done in a single pass or multiple passes through the gamma irradiation sterilizer. For example, exposing the wound dressing to 5 sterilization cycles using a dose of 5 kGy per cycle would be similar to exposing the wound dressing to one dose of 25 kGy of gamma irradiation. Due to labor and time constraints, it is generally desirable to minimize the number of passes that a wound dressing experiences through the gamma irradiation sterilizer. Typically, it is desirable that the number of passes through the sterilizer be five or less, and it may be even more desirable for the number of passes to be two or less. Exposure time may be viewed as the time a sample to be sterilized is exposed to the gamma radiation. Typically the exposure time is on the order of hours.

Gamma radiation is a suitable method to sterilize the wound dressings of this disclosure. Exposure of the wound dressings of this disclosure to a suitable level gamma irradiation does not produce a comparable loss of re-epithelialization performance.

The ability to use terminal sterilization can provide an advantage over other forms of wound dressings that include, for example, a liquid. Without being bound by theory, aqueous solutions or suspensions of proteins such as fibrinogen and thrombin can be expected to undergo inter-chain crosslinking during terminal sterilization that involves gamma-irradiation. In a dry format, a protein will often undergo chain scission (i.e., degradation) and thereby lose enzymatic activity. Thus, gamma-irradiation of the reagents for a polymerization (e.g., fibrinogen and/or thrombin) may result in crosslinking and/or chain scission of the separate reagents, and thus no reaction (or no polymerization) to form fibrin. Depending on the level of gamma-irradiation, fibrin may also undergo some chain scission, although even with low levels of degradation, the gamma-irradiated fibrin still can be recognized by cells to obtain the desired re-epithelialization effect.

The (e.g. dehydrated) fibrin hydrogel in its various physical forms can be utilized for the treatment of wounds. Thus, in another embodiment, a method of treatment of a (e.g. mammal or human) wound is described providing the fibrin composition as described herein or a wound dressing comprising the described fibrin composition and providing the fibrin composition proximate a wound. In typical embodiments, the fibrin-containing layer (e.g. sheet, foam, particles) is in direct contact with at least a portion or portions of the wound. Alternatively, it is surmised that the fibrin-containing layer may be in close proximity, yet not in direct contact. For example, it is contemplated that an absorbent porous carrier layer, such as a gauze, may comprise the fibrin-containing layer on the opposing surface as the wound facing surface. During use fluids of the wound penetrate through the absorbent porous carrier layer thereby solubilizing the fibrin-containing layer.

The fibrin composition has been shown to increase the rate of re-epithelialization in both in-vivo porcine studies and in-vitro studies using human primary isolated cells. In some embodiments, the re-epithelialization was 2 times faster than the control (same dressing without (e.g. dehydrated) fibrin hydrogel).

The dehydrated fibrin composition was also been found to affect the formation of pro-healing and anti-healing biomarkers such as growth factors, proteases, cytokines as commonly known in the art. (See Murphy, K. (2012). Janeway's Immunobiology (E. Lawrence Ed. 8th ed.): Garland science). In some embodiments, the formation of VEGF—vascular endothelial growth factor was at least 1, 2, 3, or 4 times greater than the control. In some embodiments, the EGF—epidermal growth factor was as least 1 or 2 times greater than the control. In some embodiments, the formation of matrix metalloproteinase—MMP1 and/or MMP8—was at least 1, 2, 3, 4, 5, 6, 7, 8, or 9 times greater than the control. In some embodiments, the formation of matrix metalloproteinase—MMP9—was at least 10, 20, 30, 40, 50, 60, 70, or 80 times greater than the control. In some embodiments, the formation of TIMP1—tissue inhibitor of metalloproteinase was at least 1, 2, 3, or 4 times greater than the control. Prohealing markers IL-4, IL-6, IL-10, EGF, FGF-basic were the same as the control, indicating no effect. Further, anti-healing biomarkers TNF-alpha, IL1-alpha, IL-1beta, IL-2 were all below the detection limit of the assay, indicating a low pro-inflammatory profile.

All patents and patent applications cites herein are incorporated by reference. Other modifications and variations to the present disclosure may be practiced by those of ordinary skill in the art, without departing from the spirit and scope of the present disclosure. It is understood that aspects of the various embodiments may be interchanged in whole or part or combined with other aspects of the various embodiments. The preceding description, given in order to enable one of ordinary skill in the art to practice the claimed disclosure, is not to be construed as limiting the scope of the disclosure, which is defined by the claims and all equivalents thereto.

EXAMPLES

Unless otherwise noted, all parts, percentages, ratios, etc. in the Examples and the rest of the specification are by weight. "Weight percent" is in some places abbreviated as "wt.-%".

Materials

HEPES, $CaCl_2$, NaCl were obtained from SIGMA-Aldrich (Milwaukee, WI). Other materials are listed as used in the Examples below.

Examples 1-3 and Comparative Examples C1-C6—Preparation of Fibrin Gel Sheets with Various Salt Concentrations Fibrin gels were cast by dissolving 2.7 g fibrinogen (SIGMA catalog number F8630, available from SIGMA-Aldrich of Milwaukee, WI) in 592.5 mL water with various salts as shown in Table 1 below, plus 1% w/w glycerol (SIGMA catalog number G2025). Next, 0.6 Units of thrombin (SIGMA catalog number T7009) per mg of fibrinogen was added to the fibrinogen solution to initiate polymerization. This solution mixture was mixed for 20-30 seconds and then transferred to a 6-well plate to finalize the polymerization. The mixture was incubated at 37° C. for 30 minutes and then evaluated qualitatively for gel formation.

If the components formed a gel, a continuous opaque white material formed in the well of the plate and that could be removed from the plate as a single mass. If the components did not form a gel, one of two failure modes was recorded. In the case of Failure Mode 1, precipitation of components was observed and the precipitated solids were surrounded by unpolymerized aqueous solution. In the case of Failure Mode 2, no differences were observed before and after combination of the components. Thus, the composition remained an aqueous ungelled solution. The post-drying salt content was determined by measuring the conductivity of a solution containing 1% w/w of a fibrin sheet dehydrated to a water content of about 10% in 18.2 megohm-cm at 25° C. water.

The moisture content was determined by calculating the weight loss of a (completely) dehydrated sample of the same film. The (completely) dehydrated sample was conditioned in a convection oven at 60° C. for 24 hours.

TABLE 1

Composition: Salt Content and Gel formulation

| EXAMPLE | NaCl (wt.-% solution) | $CaCl_2$ (wt.-% solution) | NaCl + $CaCl_2$ (Total wt.-% solution) | Gel formation | Post-drying salt content |
|---|---|---|---|---|---|
| EX. 1 | 0.9 | 0.333 | 1.233 | Yes | 41.89 wt.-% |
| EX. 2 | 0.9 | 0.033 | 0.933 | Yes | 35.31% |
| EX. 3 | 0.9 | 0.003 | 0.903 | Yes | 34.57% |
| C1 | 0.09 | 0.333 | 0.423 | No (1) | 19.83% |
| C2 | 0 | 0.333 | 0.333 | No (1) | 16.30% |
| C3 | 0.09 | 0.033 | 0.123 | No (2) | 6.73% |
| C4 | 0.09 | 0.003 | 0.093 | No (2) | 5.18% |
| C5 | 0 | 0.033 | 0.033 | No (2) | 1.91% |
| C6 | 0 | 0.003 | 0.003 | No (2) | 0.19% |

Example 4—Preparation of Fibrin Gel Sheets for In-Vivo Studies

Fibrin gels were cast by dissolving 2.7 g fibrinogen (SIGMA catalog number F8630) in 592.5 mL of 20 mM HEPES, pH 7.4 (AMRESCO catalog number 0511) in 0.9% NaCl, plus 1% w/w glycerol (SIGMA catalog number G2025). To this solution, 2.0 g $CaCl_2$ (SIGMA catalog number C5670) was added. Next, 0.06 Units of thrombin (SIGMA catalog number T7000) per mg of fibrinogen (resulting in a thrombin concentration of 0.27 U/mL) was added to the fibrinogen solution to initiate polymerization. This solution was mixed for 20-30 seconds and then cast into a lyophilizer pan (10 inch×14 inch×1 inch, 316L stainless steel pan having a stainless steel thickness of 0.060") resulting in a gel that was approximately 7 mm thick. The gel was incubated at 37° C. for 30-60 minutes. The fibrin hydrogel prior to dehydration had a fibrin content of about 0.45 wt.-%, a salt content of about 0.6 wt. %, a glycerol content of about 1%, and the remainder water (about 98%).

The fibrin hydrogel was then placed into a solution of ultra-pure water (18.2 megohm-cm at 25° C.) and 1% w/w glycerol. The volume of this solution was 10 times greater than the volume of the gel. The gel was rinsed in this solution overnight, then placed back into the lyophilizer pan from which it was cast. The lyophilizer pan was lined with a woven nylon fabric commercially available from 3M as 3M Tegoderm™ Non-Adherent Contact Layer, Product No. 5644. The gel was then freeze-dried using standard methods. The woven nylon fabric was removed from the dried gel. The resulting sheet was a flexible fibrin gel sheet with a thickness of approximately 50 micrometers. The resulting rinsed dehydrated film of fibrin gel had a fibrin content of about 50 wt.-%, a glycerol content of about 30 wt.-% and a water content of about 10 wt.-%. The resulting rinsed dehydrated film of fibrin gel sheet was found to have a salt content of approximately 10%, as determined by measuring the conductivity of a solution containing 1% w/w of the fibrin sheet in 18.2 megohm-cm at 25° C. water. The sheet was then cut into 5 cm×7.6 cm sections to be used for in vivo, partial-thickness wound studies using a porcine model.

Example 4—In-Vivo Testing Protocol

In-vivo testing of the fibrin gel sheet consisted of a 6-pig study with a 72-hr endpoint, partial-thickness wound studies using a porcine model. There were 6 wounds per pig, each 5 cm×7.6 cm (2×3 inch) in area and 500 micrometers deep. Testing was conducted using an IACUC approved protocol and care was taken to ensure proper animal treatment and minimize unnecessary pain.

On the day of wound creation, the wound area was shaved and prepped for sterile surgery. Wound areas were marked with a sterile marker and sterile mineral oil was placed over the wound area to facilitate the dermatome procedure. After wound creation, absorbent gauze was applied with light pressure for 5 minutes to achieve hemostasis. The wound margins were then painted with a benzoin tincture to improve adherence of adhesive bandages. Wounds were treated either with the fibrin gel sheet of Example 4 and then covered with 3M TEGADERM HP FOAM DRESSING (3M catalog number 90601) or controls were covered with only the 3M TEGADERM HP FOAM DRESSING (no fibrin gel sheet), considered a standard of care for wounds. When individual dressings were in place, the edges were taped down using 3M 1363 Veterinary Elastic Adhesive Tape. Then all wounds were covered with an organza cloth overlay.

At the conclusion of the study, the animal was euthanized according to approved protocols. Tissue samples were then collected for histology and biochemical analysis. Histology samples were placed into 10% neutral buffered formalin (Thermo Scientific catalog number 534801) for fixation.

Samples were then prepped for paraffin embedding, microtomed to 6 micrometers sections and stained with hematoxylin and eosin (H&E).

Example 4: In-Vivo Evaluation Results

The H&E samples were analyzed for percent re-epithelialization by measuring the width of the wound covered with keratinocytes and dividing that value by the measured width of the wound. Wounds treated with the fibrin gel sheet of Example 4 exhibited 49.8±4.9% re-epithelialization rate and the foam dressing control exhibited a re-epithelialization rate of 23.8±4.1% (mean±95% confidence interval, n=16). The conclusion was that treatment with a lyophilized fibrin gel sheet of Example 4, resulted in approximately 2 times faster re-epithelialization compared to standard of care (the foam dressing control).

Example 4: Biochemical Indications of Wound Healing

In addition to percent re-epithelialization, tissue samples of wounds treated with Example 4 and the foam dressing control were also analyzed for biomarkers. Wounds were biopsied following the fibrin gel sheet treatment for 72 hr. Wound biopsies were homogenized with a blender and analyzed for wound healing and inflammatory biomarkers. A multiplex ELISA assay was used to determine pro-healing and anti-healing wound outcomes. Selected screening panel included the following: (A) Pro-healing biomarkers: IL-4, IL-6, IL-10, EGF, FGF-basic, VEGF, MMP-1, MMP-3, MMP-8, MMP-9, TIMP-1; and (B) Anti-healing biomarkers: TNF-alpha, IL1-alpha, IL-1beta, IL-2. The data shown in TABLE 2 are representative of 4 animals with 2 biopsies of 2 wounds for each treatment. TABLE 2 shows results for the biomarkers of wound healing, summarized as X-fold increase over the control (3M TEGADERM HP FOAM DRESSING) in Example 4. The results indicate significant changes observed with fibrin treatment compared to the standard of care (control), as well as trends (greater than 5 fold up-regulation) of fibrin mediated biomarker induction, indicative of wound healing. The anti-healing biomarkers tested were all below the detection limit of the assay (data not shown), indicating a low pro-inflammatory profile and further confirming the capability of the fibrin gel sheet of Example 4 to accelerate the wound healing process toward completion. Statistical significance was determined via student's t-test where significance was determined at p<0.05.

TABLE 2

EXAMPLE 4: WOUND HEALING BIOMARKER ANALYSIS

| Biomarker | X-Fold Change in up-regulation Example 4 fibrin treatment vs control | |
|---|---|---|
| | Average ± std. dev. | p-value |
| VEGF | 4.3 ± 0.9 | 0.0005 |
| EGF | 2.1 ± 0.03 | 0.0005 |
| MMP1 | 8.9 ± 11.9 | ns |
| MMP8 | 6.4 ± 4.9 | 0.034 |
| MMP9 | 75.6 ± 4.63 | ns |
| TIMP-1 | 3.45 ± 2.05 | 0.019 |

Example 4: Mechanical Testing and Results

The fibrin gel sheets of Example 4 (after removal of the woven nylon fabric) were tested for mechanical properties using an INSTRON Tensile Tester Model 5943 with a 5 kg-force load cell. The dried (lyophilized) gel sheets of Example 4 was cut to a width of 6.2 mm. Thickness of the gel sheets was measured by micrometer to determine cross-sectional area of tested samples. The tensile testing apparatus was calibrated for grip spacing at each measurement. Samples were mounted between tensile grip adapters and elongated at a rate of 50 mm/min. Data acquisition was triggered at 0.02 N of applied force. Resulting strain was calculated in situ using the cross-sectional area defined by the input sample measurements for each test. Young's Modulus was calculated from the linear region of the stress-strain curve and defined as between 0.2% and 2% strain.

TABLE 3

EXAMPLE 4: MECHANICAL TESTING RESULTS

| Example 4 | Ultimate Tensile Strength (MPa) | Young's Elastic Modulus (MPa) | % Elongation | Thickness (microns) | Basis Weight (mg/cm$^2$) | Density* |
|---|---|---|---|---|---|---|
| Dried fibrin gel sheet | 3.41 +/− 0.79 | 32.9 +/− 2.53 | 75.2 +/− 26.7 | 44.7 ± 1.9 | 4.12 | 922 mg/cm$^3$ |

*Calculated based on thickness and basis weight.

Example 5—Alternative Drying Methods for Fibrin Gel Sheet Preparation

Fibrin gel sheets were prepared by the same method described in Example 4. The only changes were (1) the source of fibrinogen and thrombin were both obtained from Cambryn Biologics LLC, of Sarasota, FL and (2) two different drying techniques were evaluated. Fibrin gel sheet samples were dried using (i) the lyophilization method as outlined above or (ii) dried in a convection oven at 60° C. for 3-5 hours. The moisture content of both films was 10% or less.

The purpose of this example was to compare oven drying to lyophilization as a method to dehydrate the fibrin gels. Oven drying of proteins is not generally an acceptable process because tertiary structure of proteins is easily lost when heated.

The oven-dried fibrin gel sheets were observed to be more transparent and more uniform than the lyophilized sheets. The lyophilized fibrin gel sheets, though similar in composition, were more opaque due to the formation of ice crystals within the sheet as part of this dehydration process. Also the fibrin gel sheet dried by lyophilization exhibited a more random variation in opacity.

Example 5—In-Vivo Testing Protocol

The in-vivo testing of the fibrin gel sheets of Example 5 was done similarly to Example 4. A 2-pig study was conducted with a 72 hour endpoint. Other than treatment groups (lyophilized fibrin gel sheet, oven-dried fibrin gel sheet, or control—3M foam dressing only), there were no differences in the protocol compared to that which was performed in Example 4.

Example 5—In-Vivo Testing Results

H&E samples were analyzed for percent re-epithelialization by measuring the width of the wound covered with keratinocytes and dividing that value by the measured width of the wound as was done in Example 4. A summary of the percent re-epithelialization results for the in-vivo testing of Example 5 samples (mean±SEM, n=4 per treatment) are shown below in TABLE 4. On average, fibrin gel sheet treatments of Example 5 exhibited 2 times more re-epithelialized than the control group (3M foam dressing only). There was no statistical difference between drying methods regarding re-epithelialization.

TABLE 4

EXAMPLE 5: Percent Re-epithelialization Results

| Wound Treatment:<br>Drying Method | % Re-epithelialization |
| --- | --- |
| Control (3M Foam Dressing) | 29.4 ± 7.4% |
| Example 5: Oven-dried Sheet | 61.1 ± 7.3% |
| Example 5: Lyophilized Sheet | 52.9 ± 9.7% |

Comparative Example C7

Comparative Example C7 was prepared to demonstrate the impact of insufficient washing on fibrin formation and the implications for wound healing, without glycerol present.

Preparation of a fibrin gel powder. A fibrin gel was first prepared using the same procedure as Example 4 with the following exceptions. The thrombin was sourced from SIGMA-Aldrich, cat. No. T6634. Also there was no glycerol added and the resulting gel was not washed. The solution for polymerization of a fibrin gel was prepared in a 50 mL centrifuge tube. The polymerized gel was lyophilized by freezing to −40° C., followed by pulling a vacuum to approximately 500 mTorr and ramping the temperature up to 20° C. while maintaining vacuum. The dried gel was then crushed into a powder by mortar and pestle.

A pressure sensitive adhesive (PSA) solution (isooctyl acrylate and acrylamide combined in a 97:3 weight ratio and dissolved at 33 wt. % solids in a solvent mixture of 51 wt. % heptane and 49 wt. % ethyl acetate (EtOAc)) was diluted 1:1 by volume in pentane. This solution was then put into an aerosolization jar, and then was sprayed onto a layer of an absorbent foam (obtained from 3M Co., St. Paul, MN, under the trade designation "3M 90600 TEGADERM FOAM DRESSING (NONADHESIVE)"), followed by drying at 50° C. for 10 minutes, to provide an adhesive coating weight of 11.5 mg/cm$^2$ on the absorbent foam. The fibrin powder (described above—unwashed and without glycerol) was dry "shaker" coated onto the resulting adhesive coated surface with a resulting fibrin powder coating weight of 3.7 mg/cm$^2$.

The gel was not washed to remove any salts; thus, the resulting dried material was 65.5% w/w salt, 28.9% fibrin and the balance water. Salt content was determined by measuring the conductivity of a solution containing 1% w/w fibrin sheet material in 18.2 megohm-cm at 25° C. water.

Comparative Example C7: In-Vivo Testing & Results

An in-vivo porcine study following the protocol set out in Example 4 was performed using the Comparative Example C7. The wound tissue treated with Comparative Example C7 was found to be highly irritated. Histology further demonstrated signs of dermal damage during the healing process in the presence of this high salt-content material, evidenced by the presence of high numbers of neutrophils throughout the dermis and collagen degradation and mineralization. As mentioned above histology sections of tissues from Examples 6 and 7 (above) did not demonstrate this effect.

Example 6 and Comparative Example C8

Example 6 and Comparative Example C8 were prepared to demonstrate the impact of insufficient washing on fibrin formation and the implications for wound healing, with glycerol present. The fibrinogen and thrombin were both obtained from Cambryn Biologics, LLC for these examples. One gel was prepared as in Example 4, but was washed twice with a volume of 18.2 megaohm-cm water with 1% glycerol that was 10 times greater than the original volume of the gel. The other gel was prepared by doubling the formulation listed in Example 4 and washing once with a volume of 18.2 megaohm-cm water with 1% glycerol that was 10 times greater than the original volume of the gel. Salt content of the prepared examples was determined by measuring the conductivity of a solution containing 1% w/w fibrin sheet material in 18.2 megohm-cm at 25° C. water. The glycerol content was determined in the finished fibrin gel sheets by liquid chromatography-mass spectrometry (LC/MS).

The fibrin gel sheet of Example 6 was prepared with extensive washing to reduce the salt concentration to 0.2% w/w and the glycerol content was 33% w/w.

The fibrin gel sheet of Comparative Example C8 was intentionally not sufficiently washed, resulting in a gel that had a salt concentration of 23.6% and a glycerol content of approximately 50%.

Example 6 and Comparative Example C8: In-Vivo Testing & Results

The gel sheets of Example 6 and Comparative Example C8 were evaluated in an in-vivo porcine study following the protocol set out in Example 4. Examination of the wounds for re-epithelialization after 3 days demonstrated that Example 6 promoted wound healing as evidenced by regions of low inflammation and coloration indicative of re-epithelialization. Histological examination of wounds treated with Example 6 showed signs of increased keratinocyte migration over the wound space. The porcine wounds treated with Comparative Example C8 showed signs of tissue damage and necrosis; the wound space became brown/black in color. Histological examination of wounds treated with Comparative Example C8 also showed apoptotic cells, cellular debris, collagen degeneration and vascular necrosis. Quantification of re-epithelialization showed that the wounds treated with Example 6 (washed formulation with lower salt content) healed approximately 2 times faster than the 3M 90600 TEGADERM FOAM DRESSING control.

Example 7—Alternative Plasticizing Components Other than Glycerol were Evaluated Fibrin gels were cast by dissolving 0.54 g fibrinogen (SIGMA-Aldrich, Cat. No. F8630) in 60 mL 20 mM HEPES buffered saline (pH 7.4) to make a stock solution. Mixtures of fibrinogen with different plasticizers were then made by adding 2% w/w plasticizer (TABLE 5) to 5 mL of the stock solution. An amount of 0.4 g CaCl$_2$ (SIGMA-Aldrich, Cat. No. C5670) was added to a solution of 1.2 U/mL thrombin. Polymerization was initiated by adding equal parts of the fibrinogen and thrombin solutions. The resulting solution was mixed for 20-30 seconds and then cast into a single well of a 6-well plate. The gel was incubated at 37° C. for 30-60 minutes and then placed into a solution of water (18.2 megohm-cm at 25° C.)+1% w/w plasticizer. The volume of this solution was 10 times greater than the volume of the gel. The gel was rinsed in this solution overnight, then placed into a 60° C. oven until dry. All of the plasticizers tested resulted in a flexible fibrin sheet.

TABLE 5

ALTERNATIVE PLASTICIZERS

| Plasticizer | Supplier | Catalog Number |
| --- | --- | --- |
| 1,3 Butanediol | TCI | B0681 |
| 1,4 Butanediol | Alfa Aesar | A11684 |
| 2,3 Butanediol | Baker Chemical | D570-07 |
| 1,2 Propanediol | Alfa Aesar | 30948 |
| D-mannitol | Alfa Aesar | 33342 |
| Xylitol | Alfa Aesar | A16944 |
| Diglycerol | Solvay | — |
| Polyglycerol-3 | Solvay | — |

Example 8

Example 8 was prepared to evaluate a fibrin gel sheet prepared with no glycerol but with adequate rinsing to reduce the salt content in the final article. Sheets were prepared for testing similarly to Example 4 with changes only in the glycerol content of the wash step. Sheets were prepared with both 0% and 1% glycerol in the wash water. After this salt removal step, samples were dried in a convection oven at 60° C. until the moisture content was 10% or less, typically achieved in 3-5 hours. Fibrin preparations that were free of plasticizer were broken into smaller, random sized flakes, typically ranging from 1 cm to about 0.1 mm. Most particles were approximately 0.5 cm to 1 cm, though they were irregularly shaped rather than controlled to a specific shape, e.g. disks, squares or the like.

Example 8: In-Vivo Testing & Results

Example 8 samples were evaluated in an in-vivo (1 pig) porcine study following the protocol set out in Example 4, with a 72 hour endpoint. Other than treatment groups, there were no differences in the protocol compared to that which was shown in Example 4. Treatment groups consisted of fibrin flakes (large pieces of fibrin sheet without plasticizer), flexible fibrin gel sheets and 3M TEGADERM Foam dressing in Example 4.

H&E samples were analyzed for percent re-epithelialization by measuring the width of the wound covered with keratinocytes and dividing that value by the measured width of the wound as performed in Example 4. A summary of the percent re-epithelialization results for the in-vivo testing of Example 8 samples (mean±SEM, n=4 per treatment) are shown below in TABLE 6.

TABLE 6

EXAMPLE 8: Percent Re-epithelialization Results

| Wound Treatment | % Re-epithelialization |
| --- | --- |
| Control 1 (3M Foam Dressing only) | 36.7 ± 2.3% |
| Example 8: Flexible Fibrin Gel Sheet (with glycerol) | 57.5 ± 5.7% |

TABLE 6-continued

EXAMPLE 8: Percent Re-epithelialization Results

| Wound Treatment | % Re-epithelialization |
| --- | --- |
| Example 8: Fibrin Flakes (no glycerol, no plasticizer) | 70.6 ± 1.4% |

Example 9: Fibrin Micro-Bead Article

A fibrin micro-bead example may be prepared in the following manner. A 1 liter vessel can be charged with 200 mL of corn oil and 200 mL of isooctane. The solution is heated to 75° C. while stirring with an overhead mixer equipped with a half-moon impeller. A solution of 40 mg/mL fibrinogen in 0.9% NaCl saline is prepared. An amount of 25 mL of the fibrinogen in saline solution and 5 mM $CaCl_2$ solution are mixed with thrombin to yield a final thrombin concentration of 5 U/mL. The protein mixture is added to the corn oil/isooctane solution before protein coagulation and mixed with the impeller such that small aqueous phase droplets are dispersed in the oil phase to form fibrin micro-beads. The size of the microbeads is estimated to range from 50-200 micrometers. The mixing and heating is continued for 6-8 h at 75° C. The fibrin micro-beads are filtered off from the oil phase. The fibrin micro-beads may then washed with excess deionized water to obtain a final salt content of 0.5% and subsequently lyophilized for 48 hours.

Example 10—Foamed Fibrin Article

A foamed fibrin article was prepared in the following manner. Fibrin gel was prepared by preparing a fibrinogen solution as in Example 4. Immediately after the addition of thrombin to initiate polymerization of fibrin, the solution was vigorously mixed for 20-30 seconds so as to aerate the solution. The resulting aerated solution was transferred to a pan to finalize the polymerization. The foam was incubated at 37° C. for 30 minutes and then placed into a solution of 18.2 megohm-cm water+1% w/w glycerol. The volume of this solution was 10 times greater than the volume of the original fibrinogen solution. As in Example 5, the foam was rinsed overnight, then transferred back into the pan from which it was cast. The foam was then freeze-dried as in Example 4. The resulting dried foam is flexible and had a salt concentration less than 5%.

Example 11: Fibrin Gel Preparation and Washing

Fibrin gels were prepared from fibrinogen obtained from Bovogen Biologicals, Australia. The Fibrinogen powder (Bovogen Biologicals, Australia) was analyzed by ion chromatography and determined to contain approximately 14 w/w % sodium citrate. It is also estimated to contain 12 w/w % sodium chloride.

Fibrin gels were prepared by dissolving 120 grams of fibrinogen (Bovogen Biologicals, Australia) into 2.8 liters of sterile water (Baxter, Deerfield, IL) in a 4 liter open container. The solution was mixed at a speed of 6500 rpm for 3 minutes. The solution was allowed to sit undisturbed in the open container until the entrapped air in the solution rose to the top, at which time all bubbles were physically removed with a scraper tool. An amount of 2000 units of thrombin (MP Biomedicals, LLC, Santa Ana, CA) were added to 204 milliliters of a 3.0 molar $CaCl_2$ (Sigma-Aldrich, Milwaukee, WI) solution. The thrombin/$CaCl_2$ solution was then added to the fibrinogen solution and stirred for 1 minute. The solution was then allowed to gel at room temperature for 1 hour.

The salt was removed from the gel by washing the gel with a mixture of 2400 milliliters of sterile water and 600 milliliters of 200 proof ethanol. The gel was mixed at 7500 rpm for 3 minutes in the water/ethanol solution to break up the gel. The gel was then allowed to sit for 30 minutes. The wash solution was then decanted off. This was step was repeated a second and third time by the same method, and also with the 3000 milliliters of 20% (v/v) ethanol/water wash solution. The gel was then allowed to sit for 30 minutes. The solid content of the fibrin gel was measured to be 14.25%, measured using a SARTORIUS Moisture Analyzer.

Example 12: Fibrin Gel Formulation with Cross-Linked PVP and HP Guar

Polyvinylpyrrolidone (PVP) (available as PLASDONE K90 POVIDONE from Ashland Inc. Covington, KY, USA) was cross-linked by treating it with a gamma irradiation dose between 100 to 200 kGy. The cross-linked PVP was hydrated in sterile water using a Cowles blade mixer. To the hydrated PVP solution was added Hydroxypropyl (HP) guar (available as JAGUAR HP-120 from Solvay Novecare) and mixed until hydrated and evenly dispersed. Polyglyercol 3 (Solvay) and triple washed fibrin gel (Example 11) were mixed into the solution. The concentrations of each formulation are listed below.

TABLE 7

| Raw Material | Example 12A | Example 12B | Example 12C |
|---|---|---|---|
| Water (%) | 69.6 | 69.6 | 69.6 |
| Ethanol (%) | 17.4 | 17.4 | 17.4 |
| XL PVP (%) | 2.47 | 3.9 | 1.82 |
| HP guar (%) | 0.13 | 0.39 | 0.78 |
| Polyglyercol 3 (%) | 4.55 | 5.46 | 3.9 |
| Fibrin (%) | 5.85 | 3.25 | 6.5 |

Example 13: Fibrin Gel with XL-PVP Coated onto Polyurethane Foam

Different coating weights of the Fibrin gel/PVP formulations of Example 12 were coated onto a sheet of low density, open cell polyurethane foam, and dried for approximately 20 minutes at 300° F. (149° C.). TABLE 8 summarizes the different example configurations made.

Example 14: In-Vivo Testing of Fibrin Coated Polyurethane Foam Dressings

Example 13 samples of fibrin gel/PVP coated on foam were tested in-vivo according to a 6-pig study with a 72-hr endpoint, partial-thickness wound studies using a porcine model. There were 6 wounds per pig, each 5 cm×7.6 cm (2×3 inch) in area and 500 micrometers deep. Testing was conducted using an IACUC approved protocol and care was taken to ensure proper animal treatment and minimize unnecessary pain. Prior to use in the in-vivo study Example 13 (and Example 17 below) samples were gamma sterilized between 45 and 55 kGy.

On the day of wound creation, the wound area was shaved and prepped for sterile surgery. Wound areas were marked with a sterile marker and sterile mineral oil was placed over the wound area to facilitate the dermatome procedure. After wound creation, absorbent gauze was applied with light pressure for 5 minutes to achieve hemostasis. The wound margins were then painted with a benzoin tincture to improve adherence of adhesive bandages. Wounds were treated with the fibrin gel/PVP coated foam dressing of Example 13 and then covered with 3M TEGADERM HP FOAM DRESSING (3M catalog number 90601). A Control was also performed using only the 3M TEGADERM HP FOAM DRESSING (no fibrin coated foam). 3M TEGADERM HP FOAM DRESSING is considered the standard of care for wounds. When individual dressings were in place, the edges were taped down using 3M 1363 Veterinary Elastic Adhesive Tape. Then all wounds were covered with an Organza cloth overlay.

At the conclusion of the study, the animal was euthanized according to approved protocols. Tissue samples were then collected for histology and biochemical analysis. Histology samples were placed into 10% neutral buffered formalin (Thermo Scientific catalog number 534801) for fixation. Samples were then prepped for paraffin embedding, microtomed to 6 micrometers sections and stained with hematoxylin and eosin (H&E).

Example 15: Re-Epithelialization Results of In-Vivo Evaluation of Example 13

The H&E samples were analyzed for percent re-epithelialization by measuring the width of the wound covered with keratinocytes and dividing that value by the measured width of the wound. Results are shown in TABLE 9.

TABLE 8

| | Example | | | | | | |
|---|---|---|---|---|---|---|---|
| | Ex. 13A | Ex. 13B | Ex. 13C | Ex. 13D | Ex. 13E | Ex. 13F | Ex. 13G |
| Coating Composition | Ex 12A | Ex 12A | Ex 12B | Ex 12B | Ex 12C | Ex 12C | Ex 12C |
| Coat weight (mg/cm$^2$) | 6.8 | 9.2 | 7.1 | 9.9 | 7.7 | 7.6 | 5.1 |
| *Dry % XL PVP | 19.0% | 19.0% | 30.0% | 30.0% | 14.0% | 14.0% | 14.0% |
| *Dry % HP Guar | 1.0% | 1.0% | 3.0% | 3.0% | 6.0% | 6.0% | 6.0% |
| *Dry % Polyglycerol 3 | 35.0% | 35.0% | 42.0% | 42.0% | 30.0% | 30.0% | 30.0% |
| *Dry % Fibrin | 45.0% | 45.0% | 25.0% | 25.0% | 50.0% | 50.0% | 50.0% |
| Total Dry % | 100.0% | 100.0% | 100.0% | 100.0% | 100.0% | 100.0% | 100.0% |

*Dry % amounts of components does not include entrained water in the hydrogel.

TABLE 9

RE-EPITHELIALIZATION RESULTS OF FIBRIN COATED PU FOAM DRESSINGS

| Fibrin on Foam Example | Fibrin Gel Coat Weight (mg/cm$^2$) | Percent Re-epithelialization | *Dry % Fibrin | *Dry % PVP | *Dry % Guar | *Dry % Polyglycerol 3 |
|---|---|---|---|---|---|---|
| Control (Foam only) | 0 | 55.0 | 0 | 0 | 0 | 0 |
| Ex. 13A | 6.8 | 60.4 | 45.0 | 19.0 | 1.0 | 35.0 |
| Ex. 13B | 9.2 | 57.0 | 45.0 | 19.0 | 1.0 | 35.0 |
| Ex. 13C | 7.1 | 55.7 | 25.0 | 30.0 | 3.0 | 42.0 |
| Ex. 13D | 9.9 | 51.3 | 25.0 | 30.0 | 3.0 | 42.0 |
| Ex. 13E | 7.7 | 58.4 | 50.0 | 14.0 | 6.0 | 30.0 |
| Ex. 13F | 7.6 | 60.8 | 50.0 | 14.0 | 6.0 | 30.0 |
| Ex. 13G | 5.1 | 62.0 | 50.0 | 14.0 | 6.0 | 30.0 |

*Dry % amounts of components does not include entrained water in the hydrogel.

Example 16: Fibrin Gel Formulation with Cross-Linked PVP and No HP Guar

Example 16 was prepared with the same procedure as Example 12 except that no HP Guar was used and the amounts of the other ingredients were as follows: 69.6% water, 17.4% ethanol, 1.3% XL PVP, 5.85% Polygycerol 3, and 5.85% Fibrin.

Example 17: Fibrin Gel with XL-PVP and No Guar Coated on Foam

Different coat weights of the fibrin gel/PVP formulation of Example 16 was coated onto the low density, open celled polyurethane foam. The coating weights of Examples 17A-17F are shown in Table 10.

Example 18: In-Vivo Testing and Evaluation Results of Examples 17a-17F

In-vivo testing and re-epithelialization evaluation of Examples 17A-17F were performed in the same manner as Example 14 and Example 15. Results are shown in TABLE 10.

TABLE 10

RE-EPITHELIALIZATION RESULTS OF FIBRIN GEL/PVP COATED PU FOAM DRESSINGS (NO GUAR)

| Fibrin on Foam Example | Fibrin Gel Coat Weight (mg/cm$^2$) | Percent Re-epithelialization | *Dry % Fibrin | *Dry % PVP | *Dry % Polyglycerol 3 |
|---|---|---|---|---|---|
| Control (Foam only) | 0 | 56.4 | 0 | 0 | 0 |
| Ex. 17A | 19.7 | 72.9 | 45.0 | 10.0 | 45.0 |
| Ex. 17B | 4.5 | 70.6 | 45.0 | 10.0 | 45.0 |
| Ex. 17C | 9.7 | 68.3 | 45.0 | 10.0 | 45.0 |
| Ex. 17D | 13.6 | 74.0 | 45.0 | 10.0 | 45.0 |
| Ex. 17E | 10.0 | 71.3 | 45.0 | 10.0 | 45.0 |
| Ex. 17F | 10.2 | 82.1 | 45.0 | 10.0 | 45.0 |

*Dry % amounts of components does not include entrained water in the hydrogel.

Example 19. pH Testing of Example 17

The pH of the fibrin gel coated onto foam dressing of Example 17 was measured by first cutting (5.1 cm×5.1 cm) samples out of the sterilized and non-sterilized fibrin gel coated foam. The coat weight of the Example 19 samples ranged from 12-19 mg/cm$^2$. The mass of the samples is shown in TABLE 11. The individual samples were then placed in glass jars with a lid and Blood Bank Saline (Thermo Scientific, Lot 683293, expiration date of February 2017) was added so that the fibrin gel was approximately 1% by weight of the total solution. The samples were allowed to sit in the saline for a minimum of 10 minutes and then the pH of the solution was measured. TABLE 11 shows the resulting pH of all of the samples tested.

TABLE 11 pH RESULTS OF EXAMPLE 19

| Example 19 | Mass of fibrin gel (g) | Volume of Added Saline (mL) | pH |
|---|---|---|---|
| Sterilized | 1.8372 | 183 | 7.20 |
| Non-sterilized | 1.7285 | 172 | 7.34 |

Example 20: Conductivity Testing of Example 17

The conductivity of the fibrin gel coated onto foam dressing of Example 17 were measured by first cutting (5.1 cm×5.1 cm) samples out of the sterilized and non-sterilized fibrin gel coated foam. The coat weight of the Example 20 samples ranged from 12-19 mg/cm$^2$. The mass of the samples are shown were recorded in Table 12. The individual samples were placed in glass jars with a lid and sterile water for irrigation (Baxter, Lot G122242, expiration date of March 2019) The amount of water added was such that the fibrin gel was approximately 1% by weight of the total solution. The samples were allowed to sit in the water for a minimum of 10 minutes and then the conductivity of the solution was measured.

TABLE 12

CONDUCTIVITY TEST RESULTS OF EXAMPLE 20

| Example 20 | Mass of fibrin gel (g) | Volume of Water (mL) | Conductivity (μs/cm) |
|---|---|---|---|
| Sterilized | 1.8265 | 182 | 18.10 |
| Non-sterilized | 1.7173 | 171 | 18.00 |

A conductivity of 18.1 μs/cm is indicative of about 0.001 wt.-% of (NaCl and/or $CaCl_2$) salt.

Example 21: Moisture Content Testing of Example 17

The moisture content of the fibrin gel coated onto foam dressing of Example 17 was measured by first cutting (3.2 cm×5.2 cm) samples out of the sterilized and non-sterilized fibrin gel coated foam. The coat weight of the Example 21 samples ranged from 12-19 mg/cm$^2$. The moisture level of the samples were measured with a Sartorius Moisture Analyzer. The results are summarized in TABLE 13.

TABLE 13

MOISTURE CONTENT TEST RESULTS OF EXAMPLE 21

| Example 21 | Moisture Content (%) |
|---|---|
| Sterilized | 6.49 |
| Non-sterilized | 7.58 |

A biological carrier comprising (e.g. PVP) polymer alone or in combination with the (e.g. polyglycercol plasticizer/swelling agent, and optionally in combination with (e.g. guar) modifying polymer can be combined with any of the low salt fibrin hydrogel compositions of Examples 1-10, as previously described. The selection of components and concentration thereof can be adjusted to optimize the percent re-epithelialization and/or other biological wound healing markers.

What is claimed is:

1. A method of forming a fibrin hydrogel composition, the method comprising:
   providing a fibrin hydrogel comprising:
      fibrin,
      water, and
      a fibrin hydrogel-forming salt present in an amount greater than 0.423 wt % with respect to the weight of the fibrin hydrogel;
   providing a carrier material comprising a water-soluble polymer, wherein the carrier material excludes water and excludes a plasticizer;
   combining the fibrin hydrogel with the carrier material to form a fibrin hydrogel mixture, such that the fibrin hydrogel is incorporated into the carrier material, the fibrin hydrogel mixture comprising the carrier material present in an amount of 0.5 wt % to about 10 wt.-% with respect to the weight of the fibrin hydrogel mixture; and
   reducing the amount of fibrin hydrogel-forming salt in the fibrin hydrogel mixture to an amount below 0.423 wt % with respect to the weight of the fibrin hydrogel, wherein the reducing forms the fibrin hydrogel composition.

2. The method of claim 1, wherein the fibrin hydrogel-forming salt comprises a calcium salt.

3. The method of claim 1, wherein the fibrin hydrogel further comprising a plasticizer.

4. The method of claim 3, wherein the plasticizer comprises a sugar alcohol, an alkane diol, or a combination thereof.

5. The method of claim 1, further comprising forming the fibrin hydrogel composition into a sheet, foam, or a plurality of pieces.

6. The method of claim 1, wherein reducing the amount of fibrin hydrogel-forming salt comprises rinsing the fibrin hydrogel mixture with an aqueous solution.

7. The method of claim 1, further comprising dehydrating the fibrin hydrogel composition to form a dehydrated fibrin hydrogel composition.

8. The method of claim 7, wherein the dehydrating comprises freeze-drying, oven drying, or a combination thereof.

9. The method of claim 7, wherein the dehydrated fibrin hydrogel composition comprises a fibrin hydrogel-forming salt in an amount no greater than 20 wt.-% with respect to the weight of the dehydrated fibrin hydrogel composition.

10. The method of claim 7, further comprising forming the dehydrated fibrin hydrogel composition into a plurality of pieces.

11. The method of claim 1, wherein the carrier material comprises a water soluble polymer characterized by a Fikentscher K-value of at least K-90.

12. The method of claim 1, wherein the water-soluble polymer comprises polymerized units of N-vinyl lactam.

13. The method of claim 1, the fibrin hydrogel further comprising a swelling agent.

14. A method of forming a fibrin hydrogel composition, the method comprising:
   providing an aqueous solution, the aqueous solution comprising:
      fibrinogen,
      a fibrin-forming enzyme, and
      a fibrin hydrogel-forming salt present in an amount greater than 0.432 wt % with respect to the weight of the aqueous solution;
   providing a carrier material comprising a water-soluble polymer, wherein the carrier material excludes water and excludes a plasticizer;
   combining the aqueous solution and the carrier material to form a fibrin hydrogel mixture, such that the aqueous solution is incorporated into the carrier material, the fibrin hydrogel mixture comprising the carrier material present in an amount of 0.5 wt % to 10 wt % with respect to the fibrin hydrogel mixture; and
   reducing the amount of fibrin hydrogel-forming salt in the fibrin hydrogel mixture below 0.432 wt %, with respect to the weight of the aqueous solution, to form the fibrin hydrogel composition.

15. A fibrin hydrogel composition prepared by a method of claim 1.

16. The fibrin hydrogel composition of claim 15, wherein the water-soluble polymer is an N-vinyl lactam polymer, or a copolymer thereof.

17. A wound dressing comprising a fibrin hydrogel composition of claim 15.

18. A dehydrated fibrin hydrogel composition prepared by a method of claim 7, the dehydrated fibrin hydrogel composition comprising:
- a fibrin hydrogel-forming salt present in an amount of no greater than 20 wt %,
- a carrier material present in an amount of 0.5 to 99 wt %, and
- water present in an amount no greater than 20 wt %.

19. The dehydrated fibrin hydrogel composition of claim 18, wherein the water-soluble polymer is an N-vinyl lactam polymer, or a copolymer thereof.

20. A wound dressing comprising a dehydrated fibrin hydrogel composition of claim 18.

\* \* \* \* \*